US011952586B2

(12) United States Patent
Offner et al.

(10) Patent No.: US 11,952,586 B2
(45) Date of Patent: Apr. 9, 2024

(54) B-CELL CULTIVATION METHOD

(71) Applicant: Hoffmann-La Roche Inc., Little Falls, NJ (US)

(72) Inventors: Sonja Offner, Penzberg (DE); Friederike Jung, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 307 days.

(21) Appl. No.: 16/888,213

(22) Filed: May 29, 2020

(65) Prior Publication Data

US 2020/0399596 A1 Dec. 24, 2020

Related U.S. Application Data

(63) Continuation of application No. PCT/EP2018/082401, filed on Nov. 23, 2018.

(30) Foreign Application Priority Data

Nov. 30, 2017 (EP) .................................... 17204575

(51) Int. Cl.
C12N 5/00 (2006.01)
C12N 5/0781 (2010.01)

(52) U.S. Cl.
CPC ........ *C12N 5/0635* (2013.01); *C12N 2500/30* (2013.01); *C12N 2501/2301* (2013.01); *C12N 2501/2302* (2013.01); *C12N 2501/2304* (2013.01); *C12N 2501/2306* (2013.01); *C12N 2501/231* (2013.01); *C12N 2501/2321* (2013.01); *C12N 2501/25* (2013.01); *C12N 2502/1107* (2013.01); *C12N 2529/00* (2013.01)

(58) Field of Classification Search
None
See application file for complete search history.

(56) References Cited

U.S. PATENT DOCUMENTS

| 7,615,220 | B2 | 11/2009 | Huang et al. |
| 7,807,415 | B2 | 10/2010 | Groen et al. |
| 2006/0051348 | A1 | 3/2006 | Gorlach et al. |
| 2006/0223183 | A1 | 10/2006 | Bates et al. |
| 2007/0269868 | A1 | 11/2007 | Jensen et al. |
| 2013/0084637 | A1* | 4/2013 | Endl ............... C07K 16/00 435/325 |
| 2016/0251621 | A1 | 9/2016 | Endl et al. |

FOREIGN PATENT DOCUMENTS

| EP | 0 488 470 A1 | 6/1992 |
| EP | 0 856 520 B1 | 4/2006 |
| WO | 84/04458 A1 | 11/1984 |
| WO | 90/03400 A1 | 4/1990 |
| WO | 93/15205 A3 | 8/1993 |
| WO | 1996/40252 | 12/1996 |
| WO | 02/14361 A3 | 2/2002 |
| WO | 02/072785 A2 | 9/2002 |
| WO | 2005/042019 A1 | 5/2005 |
| WO | 2007/031550 A2 | 3/2007 |
| WO | 2008/045140 A1 | 4/2008 |
| WO | 2008/144763 A2 | 11/2008 |
| WO | 2011/147903 A1 | 12/2011 |
| WO | 2013/076139 A1 | 5/2013 |
| WO | 2015/181098 A1 | 12/2015 |
| WO | 2017/167714 A1 | 10/2017 |

OTHER PUBLICATIONS

Kim et al. Pretreatment of Low Dose Radiation Reduces Radiation-Induced Apoptosis in Mouse Lymphoma (EL4) Cells. Arch. Pharm. Res. vol. 20, No. 3, pp. 212-217, 1997.*
International Preliminary Report on Patentability—PCT/EP2018/082401 (dated Jun. 2, 2020),:pp. 1-8 (Jun. 11, 2020).
International Search Report for PCT/EP2018/082401 dated Feb. 200, 2019.
Kwekkeboom, J. et al., "An efficient procedure for the generation of human monoclonal antibodies based on activation of human B lymphocytes by a murine thymoma cell line" J Immunol Meth 160(1):117-127 (Jan. 1, 1993).
Llames, S., et al., "Feeder Layer Cell Actions and Applications" Tissue Eng: Part B Rev 21(4):345-353 (Aug. 1, 2015).
Masri, S., et al., "Cloning and expression in *E. coli* of a functional Fab fragment obtained from single human lymphocyte against anthrax toxin" Molec Immunol 44(8):2101-2106 (Mar. 1, 2007).
Paus, D., et al., "Antigen recognition strength regulates the choice between extrafollicular plasma cell and germinal center B cell differentiation" J Exp Med 203(4):1081-1091 (Apr. 17, 2006).
Pike et al., "A high-efficiency cloning system for single hapten-specific B lymphocytes that is suitable for assay of putative growth and differentiation factors" Proc. Nati. Acad. Sci. USA 82:3395-3399 ( 1985).
Roy, A., et al., "Increased Efficiency of g-Irradiated versus Mitomycin C-Treated Feeder Cells for the Expansion of Normal Human Cells in Long-Term Cultures" J Hematother Stem Cell Res 10(6):873-880 (Dec. 1, 2001).
Smith, K., et al., "The extent of affinity maturation differs between the memory and antibody-forming cell compartments in the primary immune response" EMBO J 16(11):2996-3006 (Jun. 2, 1997).
Steenbakkers et al., "Efficient generation of human anti-cytomegalovirus IgG monoclonal antibodies from preselected antigen-specific B cells" Human Antibodies 4(4):166-173 ( 1993).
Steenbakkers, et al., "A new approach to the generation of human or murine antibody producing hybridomas" Journal of Immunological Methods 152:69-77 ( 1992).
Tucci et al., "Effects of Eleven Cytokines and OF IL-1 and Tumor Necrosis Factor Inhibitors in a Human B Cell Assay" J Immunol 148(9):2778-2784 (May 1992).
Weitkamp, J., et al., "Generation of recombinant human monoclonal antibodies to rotavirus from single antigen-specific B cells selected with fluorescent virus-like particles" J Immunol Meth 275(1-2):223-237 (Apr. 1, 2003).

(Continued)

Primary Examiner — Nianxiang Zou
(74) Attorney, Agent, or Firm — Hoffmann-La Roche Inc.

(57) ABSTRACT

Herein is reported a method for the co-cultivation of single deposited B-cells, which can be of any source, with EL-4 B5 feeder cells in a suitable co-cultivation medium. In the herein reported methods the EL-4 B5 cells have been irradiated with a dose of less than 40 Gy, preferably 9.5 Gy or less. Thereby the EL-4 B5 cells have a higher viability and maintain the ability to divide in cultivation at doses less than 6 Gy.

20 Claims, 10 Drawing Sheets

Specification includes a Sequence Listing.

(56) References Cited

OTHER PUBLICATIONS

Wrammert, J., et al., "Rapid cloning of high-affinity human monoclonal antibodies against influenza virus" Nature 453(7195):667-672 (May 29, 2008).
Zubler et al., "Activated B cells express Receptors for, and proliferate in response to, pure Interleukin 2" J Exp Med 160:1170-1183 (Oct. 1984).
Zubler, R.,, "Polyclonal B cell responses in the presence of defined filler Cells: Complementary effects of lipopolysaccharide and anti-immunoglobulin antibodies" Eur J Immunol 14(4):357-363 (Apr. 1, 1984).
Chen et al., "Roles of CD40 System in Activation of B Lymphocytes" Int. J. of Immunol. (With EN translation), 1:17-21 (1996).

* cited by examiner

```
                        SEQUENCE LISTING

<160> NUMBER OF SEQ ID NOS: 5

<210> SEQ ID NO 1
<211> LENGTH: 4
<212> TYPE: PRT
<213> ORGANISM: Homo sapiens

<400> SEQUENCE: 1

Glu Val Gln Leu
1

<210> SEQ ID NO 2
<211> LENGTH: 4
<212> TYPE: PRT
<213> ORGANISM: Homo sapiens

<400> SEQUENCE: 2

Gln Val Gln Leu
1

<210> SEQ ID NO 3
<211> LENGTH: 4
<212> TYPE: PRT
<213> ORGANISM: Homo sapiens

<400> SEQUENCE: 3

Asp Ile Val Met
1

<210> SEQ ID NO 4
<211> LENGTH: 4
<212> TYPE: PRT
<213> ORGANISM: Homo sapiens

<400> SEQUENCE: 4

Asp Ile Gln Met
1

<210> SEQ ID NO 5
<211> LENGTH: 5
<212> TYPE: PRT
<213> ORGANISM: Homo sapiens

<400> SEQUENCE: 5

Lys Leu Glu Ile Lys
1               5
```

B-CELL CULTIVATION METHOD

CROSS-REFERENCE TO RELATED APPLICATIONS

This application is a continuation of International Application No. PCT/EP2018/082401, filed Nov. 23, 2018, which claims benefit to European Patent Application No. 17204575.9, filed Nov. 30, 2017; all of which are incorporated by reference in their entirety.

SEQUENCE LISTING

This application contains a Sequence Listing which has been submitted via EFS-Web and is hereby incorporated by reference in its entirety. Said ASCII copy, created on May 26, 2020, is named P34496-US_Sequence_Listing.txt and is 815 bytes in size.

FIELD OF THE INVENTION

Herein are reported methods for co-cultivating B-cells with EL-4 B5 feeder cells, wherein the EL-4 B5 cells have been irradiated with a dose of less than 10 Gy.

BACKGROUND OF THE INVENTION

For obtaining cells secreting monoclonal antibodies the hybridoma technology developed by Koehler and Milstein is widely used. But in the hybridoma technology only a fraction of the B-cells obtained from an immunized experimental animal can be fused and propagated. The source of the B-cells is generally an organ of an immunized experimental animal such as the spleen.

Zubler et al. started in 1984 to develop a different approach for obtaining cells secreting monoclonal antibodies (see e.g. Eur. J. Immunol. 14 (1984) 357-63, J. Exp. Med. 160 (1984) 1170-1183). Therein the B-cells are obtained from the blood of the immunized experimental animal and co-cultivated with murine EL-4 B5 feeder cells in the presence of a cytokine comprising feeder mix. With this methodology up to 50 ng/ml antibody can be obtained after 10-12 days of co-cultivation.

Weitkamp, J-H., et al., (J. Immunol. Meth. 275 (2003) 223-237) report the generation of recombinant human monoclonal antibodies to rotavirus from single antigen-specific B-cells selected with fluorescent virus-like particles. A method of producing a plurality of isolated antibodies to a plurality of cognate antigens is reported in US 2006/0051348. In WO 2008/144763 and WO 2008/045140 antibodies to IL-6 and uses thereof and a culture method for obtaining a clonal population of antigen-specific B cells are reported, respectively. A culture method for obtaining a clonal population of antigen-specific B-cells is reported in US 2007/0269868. Masri et al. (in Mol. Immunol. 44 (2007) 2101-2106) report the cloning and expression in *E. coli* of a functional Fab fragment obtained from single human lymphocyte against anthrax toxin. A method for preparing immunoglobulin libraries is reported in WO 2007/031550. Generally, the employed feeder cells are irradiated to inhibit their growth.

In WO 84/04458 monoclonal antibodies reactive with endotoxin core are disclosed.

Pike, B. L. and Nossal, G. J. V., reported a high-efficiency cloning system for single hapten-specific B lymphocytes that is suitable for assay of putative growth and differentiation factors (Proc. Natl. Acad. Sci. USA 82 (1985) 3395).

In EP 0 488 470 a method for the production of antibodies is disclosed. In WO 90/003400 intercellular adhesion molecules, and their binding ligands are disclosed. Steenbakkers, P. G. A., et al., reported a new approach to the generation of human or murine antibody producing hybridomas (J. Immunol. Meth. 152 (1992) 69-77). In WO 93/15205 a synthetic *Haemophilus influenzae* conjugate vaccine is disclosed.

Steenbakkers, P. G., et al., reported the efficient generation of human anti-cytomegalovirus IgG monoclonal antibodies from preselected antigen-specific B cells (Hum. Antibody. Hybridom. 4 (1993) 166-173).

In EP 0 856 520 a method of preparing a monoclonal antibody, pharmaceutical composition and a diagnostic reagent are disclosed. In WO 02/14361 nucleic acids and corresponding proteins entitled 83P2H3 and CaTrF2E11 useful in treatment and detection of cancer are disclosed. In WO 02/072785 nucleic acid and corresponding protein entitled 125P5C8 useful in treatment and detection of cancer are disclosed.

In WO 2005/042019 anti-thymocyte antiserum and use thereof to trigger B-cell apoptosis are disclosed. In WO 2011/147903 a single B-cell cultivation method is reported. In U.S. Pat. No. 7,807,415 methods for producing stable immortalized B-lymphocytes are reported.

WO 2017/167714 discloses a method for the co-cultivation of single deposited B-cells, which can be of any source, with feeder cells in a suitable co-cultivation medium.

SUMMARY OF THE INVENTION

Herein is reported a method for the co-cultivation of single deposited B-cells, which can be of any source, with EL-4 B5 feeder cells in a suitable co-cultivation medium. In the herein reported methods the EL-4 B5 cells have been irradiated with a dose of less than 10 Gy, preferably 6 Gy or less. Thereby the EL-4 B5 cells maintain the ability to divide in cultivation with a high viability. Thus, it is advisable in order to prevent the overgrowth of the single B-cells and its progeny by the dividing EL-4 B5 cells to reduce the cell number of the EL-4 B5 cells, especially when a low irradiation dose is used.

The method according to the invention is used as one of the first steps during the generation of therapeutic antibodies.

The method according to the invention can be used with any B-cells of any origin, such as e.g. blood or spleen, or from any animal, such as e.g. rabbit, mouse, rat, sheep or human-transgenic animals. If the source is a human-transgenic animal the antibody produced by the B-cells identified and isolated with a method according to the current invention might be directly used for clinical trials.

The invention is based at least in part on the finding that the dose for the irradiation of EL-4 B5 feeder cells that are to be used in the co-cultivation with single deposited B-cells can be reduced to 0 to 9.5 Gy without interfering with the purpose of the EL-4 B5 feeder cells to stimulate the growth of co-cultivated B-cells.

The invention is based at least in part on the finding that when using EL-4 B5 cells pre-treated with a lower irradiation dose of 0 Gy to 9.5 Gy, i.e. 9.5 Gy or less, in a co-cultivation method with (single deposited) B-cells the IgG production of the B-cells can be increased.

The invention is based at least in part on the finding that when using EL-4 B5 cells pre-treated with an irradiation dose of about 4 Gy in a co-cultivation method with (single deposited) B-cells amongst other things the number of IgG-positive wells can be increased.

The invention is based at least in part on the finding that it is also possible to use non-irradiated EL-4 B5 cell in a co-cultivation method with (single deposited) B-cells.

The invention is based at least in part on the finding that by reducing the irradiation dose of the feeder cells a reduced number of feeder cells is required for the co-cultivation. The feeder cells by themselves have to be produced also. This is done in an additional cultivation prior to the irradiation. By reducing the number of feeder cells required per co-cultivation an increased number of co-cultivations can be inoculated from the same feeder cell cultivation. Thereby the hands-on-time and costs are reduced. Likewise, as the feeder cells are more viable, the amount of feeder mix can be reduced which also reduces the associated costs.

The invention is based at least in part on the finding of the interrelation between irradiation dose of EL-4 B5 feeder cells i) with number of cells required in a co-cultivation, ii) with single deposited B-cells with concentration of the required feeder mix, iii) with productivity and number of IgG-positive cultivations, as well as iv) time and costs.

This results amongst other things in a reduction of the required non-irradiated EL-4 B5 cell numbers and thereby of the associated costs of goods.

The individual aspects as reported herein are methods for
i) the isolation of a B-cell or a B-cell clone from a population of B-cells, whereby the isolated B-cell or B-cell clone produces an antibody specifically binding to a target,
ii) the co-cultivation of single deposited B-cells, and
iii) the production of an antibody.

Concomitantly with the methods also the corresponding uses are also encompassed and disclosed.

One aspect as reported herein is a method for co-cultivating one or more B-cells comprising the step of
  co-cultivating one or more B-cells with EL-4 B5 cells,
  whereby the EL-4 B5 cells have been irradiated prior to the co-cultivation with a dose of 9.5 Gy or less.

In one embodiment the method comprises the steps of combining one or more B-cells with EL-4 B5 cells, and co-cultivating the one or more B-cells with the EL-4 B5 cells.

In one embodiment the number of EL-4 B5 cells (at the start of the co-cultivation) is less than $5 \times 10^4$ per B-cell.

In one embodiment the irradiation is with a dose of 9.5 Gy or less and more than 0 Gy.

In one embodiment of the method according to the invention the number of EL-4 B5 cells is less than $1 \times 10^4$ EL-4 B5 cells per B-cell (whereby in this embodiment the irradiation is with 0 Gy). In one embodiment the number of EL-4 B5 cells is less than $7.5 \times 10^3$ EL-4 B5 cells per B-cell.

In one embodiment of the method according to the invention the co-cultivating is additionally in the presence of a feeder mix.

In one embodiment the feeder mix (cytokine mix, CM) comprises one or more of
  i) interleukin-1 beta and tumor necrosis factor alpha,
  ii) interleukin-2 (IL-2) and/or interleukin-10 (IL-10),
  iii) *Staphylococcus aureus* strain Cowan's cells (SAC),
  iv) interleukin-21 (IL-21) and optionally interleukin-2 (IL-2),
  v) B-cell activation factor of the tumor necrosis factor family (BAFF),
  vi) interleukin-6 (IL-6),
  vii) interleukin-4 (IL-4), and
  viii) thymocyte cultivation supernatant.

In one embodiment the feeder mix comprises
  up to about 2 ng/ml (murine) IL-1beta,
  up to about 2 ng/ml (murine) TNFalpha,
  up to about 50 ng/ml (murine) IL-2,
  up to about 10 ng/ml (murine) IL-10, and
  up to about 10 ng/ml (murine) IL-6,
  or a fraction thereof.

In one embodiment the feeder mix comprises
  up to about 2 ng/ml with $5.5\text{-}14 \times 10^8$ IU/mg (murine) IL-1beta,
  up to about 2 ng/ml with $2.3\text{-}2.9 \times 10^8$ U/mg (murine) TNFalpha,
  up to about 50 ng/ml with 6-7 (preferably 6.3)$\times 10^6$ IU/mg (murine) IL-2,
  up to about 10 ng/ml with $6\text{-}7.5 \times 10^5$ IU/mg (murine) IL-10, and
  up to about 10 ng/ml with $9.2\text{-}16.1 \times 10^8$ U/mg (murine) IL-6,
  or a fraction thereof.

Thus, the concentrations are upper limits.

In one embodiment the fraction of the feeder mix is in the range of from 1.0- to 0.015-times of each of said concentrations of IL-1beta, TNFalpha, IL-2, IL-10, and IL-6.

In one embodiment the fraction of the feeder mix is selected from the group of fractions consisting of 0.75-, 0.5-, 0.32-, 0.25-, 0.1-, 0.066-, 0.032-, 0.015-, 0.01-, 0.0075-, and 0.0038-times of each of said concentrations of IL-1beta, TNFalpha, IL-2, IL-10, and IL-6.

In one embodiment the feeder mix further comprises about 0.01 ng/ml-1.0 ng/ml phorbol myristate acetate (PMA). In one embodiment the feeder mix further comprises about 0.01 ng/ml to 0.5 ng/ml phorbol myristate acetate.

In one embodiment the method for co-cultivating one or more B-cells comprising the step of
  co-cultivating one or more B-cells with EL-4 B5 cells in the presence of a feeder mix,
  wherein the EL-4 B5 cells have been irradiated prior to the co-cultivation with a dose of 9.5 Gy or less,
  wherein the number of EL-4 B5 cells (at the beginning of the co-cultivating) is less than $4 \times 10^4$ EL-4 B5 cells per B-cell,
  wherein the feeder mix feeder mix comprises
    up to about 2 ng/ml with $5.5\text{-}14 \times 10^8$ IU/mg (murine) IL-1beta,
    up to about 2 ng/ml with $2.3\text{-}2.9 \times 10^8$ U/mg (murine) TNFalpha,
    up to about 50 ng/ml with 6-7 (preferably 6.3)$\times 10^6$ IU/mg (murine) IL-2,
    up to about 10 ng/ml with $6\text{-}7.5 \times 10^5$ IU/mg (murine) IL-10, and
    up to about 10 ng/ml with $9.2\text{-}16.1 \times 10^8$ U/mg (murine) IL-6,
    or a fraction of 0.75-, 0.5-, 0.32-, 0.25-, 0.1-, 0.066-, 0.032-, 0.015-, 0.01-, 0.0075-, or 0.0038-times of each of said concentrations of IL-1beta, TNFalpha, IL-2, IL-10, and IL-6,
  and
  wherein the feeder mix further comprises about 0.01 ng/ml-1.0 ng/ml phorbol myristate acetate.

In one embodiment the feeder mix comprises *Staphylococcus aureus* strain Cowan's cells (SAC) and thymocyte cultivation supernatant.

In one embodiment the method is for the co-cultivation of one B-cell. In one preferred embodiment the one B-cell is a single deposited B-cell.

In one embodiment the co-cultivating is for 5 to 10 days. In one preferred embodiment the co-cultivating is for about 7 days.

One aspect as reported herein is a method for increasing the productivity of one or more B-cells comprising the step of
co-cultivating one or more B-cells with EL-4 B5 cells in the presence of a feeder mix,
wherein the EL-4 B5 cells have been irradiated prior to the co-cultivation with a dose of 9.5 Gy or less,
wherein the number of EL-4 B5 cells (at the beginning of the co-cultivating) is less than $4 \times 10^4$ EL-4 B5 cells per B-cell,
wherein the feeder mix feeder mix comprises depending on the irradiation does a fraction of 0.75-, 0.5-, 0.32-, 0.25-, 0.1-, 0.066-, 0.032-, 0.015-, 0.01-, 0.0075-, or 0.0038-times of each of the following concentrations of IL-1beta, TNFalpha, IL-2, IL-10, and IL-6
about 2 ng/ml with $5.5\text{-}14*10^8$ IU/mg (murine) IL-1beta,
about 2 ng/ml with $2.3\text{-}2.9*10^8$ U/mg (murine) TNFalpha,
about 50 ng/ml with 6-7 (preferably $6.3)*10^6$ IU/mg (murine) IL-2,
about 10 ng/ml with $6\text{-}7.5*10^5$ IU/mg (murine) IL-10, and
about 10 ng/ml with $9.2\text{-}16.1*10^8$ U/mg (murine) IL-6,
and wherein the feeder mix further comprises about 0.01 ng/ml-1.0 ng/ml phorbol myristate acetate.

One aspect as reported herein is a method for increasing the number of IgG-positive wells of single deposited and cultivated B-cells comprising the step of
co-cultivating one or more B-cells with EL-4 B5 cells in the presence of a feeder mix,
wherein the EL-4 B5 cells have been irradiated prior to the co-cultivation with a dose of 9.5 Gy or less,
wherein the number of EL-4 B5 cells (at the beginning of the co-cultivating) is less than $4 \times 10^4$ EL-4 B5 cells per B-cell,
wherein the feeder mix feeder mix comprises depending on the irradiation does a fraction of 0.75-, 0.5-, 0.32-, 0.25-, 0.1-, 0.066-, 0.032-, 0.015-, 0.01-, 0.0075-, or 0.0038-times of each of the following concentrations of IL-1beta, TNFalpha, IL-2, IL-10, and IL-6
about 2 ng/ml with $5.5\text{-}14*10^8$ IU/mg (murine) IL-1beta,
about 2 ng/ml with $2.3\text{-}2.9*10^8$ U/mg (murine) TNFalpha,
about 50 ng/ml with 6-7 (preferably $6.3)*10^6$ IU/mg (murine) IL-2,
about 10 ng/ml with $6\text{-}7.5*10^5$ IU/mg (murine) IL-10, and
about 10 ng/ml with $9.2\text{-}16.1*10^8$ U/mg (murine) IL-6,
and wherein the feeder mix further comprises about 0.01 ng/ml-1.0 ng/ml phorbol myristate acetate.

One aspect as reported herein is a method for producing an antibody comprising the co-cultivation method as reported herein.

All methods and uses as reported herein comprise the step of
(individually) co-cultivating (each single deposited or a pool of) B-cell(s) with feeder cells in a co-cultivation medium, which has been supplemented with a feeder mix.

The result of the co-cultivation is a B-cell clone, i.e. a population of B-cells that are the progeny of a single B-cell.

In one embodiment the method as reported herein further comprises prior to the co-cultivating step the following step:
depositing those B-cells of a population of B-cells that has been contacted with one to three fluorescently labelled anti-B-cell surface marker antibodies based on the antibodies and thereby fluorophores bound and/or not-bound to the B-cells as single B-cells.

In one embodiment the method as reported herein further comprises prior to the co-cultivating step the following step:
depositing those B-cells of a population of B-cells that has been contacted with two to four antibodies each specifically binding to a different B-cell surface antigen, that are labelled with one to three fluorescence dyes as single cells, whereby each antibody is conjugated to a different fluorescent dye.

The labeling is in one embodiment by contacting the B-cell population (sequentially or simultaneously) with two to four fluorescently labeled antibodies. Thereby a labeled B-cell preparation is obtained. Each of the fluorescently labeled antibodies binds to a different B-cell surface marker/target.

The depositing is by introducing the labeled B-cell preparation into a flow cytometer and depositing those cells as single cells that have been labeled with one to three fluorescent labels. As it is possible to incubate the cells with more fluorescent dyes as those which are used for selecting the cells in the cell sorter the cells can be selected for the presence of specific surface markers and (optionally) simultaneously for the absence of other surface markers.

The labeling and single cell deposition is done in order to reduce the complexity of the B-cell population by depleting those B-cells that are not likely to produce an antibody having the intended characteristics. The labeled antibodies bind to a specific polypeptide displayed on the surface of B-cells and, thus, provide for a positive selection label. Likewise, it is also possible to select cells that are only labeled with a reduced number of fluorescent dyes compared to the number of labeled antibodies with which the B-cell had been incubated, such as e.g. cells having one fluorescent label out of two (i.e. incubation with two fluorescently labelled antibodies has been performed but only one thereof binds to the B-cells). Based on the binding/non-binding of the fluorescently labeled antibodies to the individual B-cells of the B-cell population it is possible to identify and separate target B-cells using a microfluidic sorting apparatus. Concomitantly with the selection also the amount of the label can be determined.

In one embodiment the method as reported herein further comprises the step of incubating the population of B-cells without feeder cells/in the absence of feeder cells in the co-cultivation medium prior to the single cell depositing/deposition. In one embodiment the incubating is at about 37° C. In one embodiment the incubating is for about 0.5 to about two hours. In one embodiment the incubating is for about one hour. In one preferred embodiment the incubating is at about 37° C. for about one hour.

In one embodiment the method as reported herein further comprises after the depositing step and before the co-cultivating step but after the addition of the EL-4 B5 feeder cells the step of centrifuging the single cell deposited B-cells. Without being bound by this theory it is assumed that thereby the physical contact between the feeder cells and the B-cell is increased. In one embodiment the centrifuging is for about 1 min. to about 30 min. In one embodiment the centrifuging is for about 5 min. In one embodiment the centrifuging is at about 100×g to about 1,000×g. In one embodiment the centrifuging is at about 300×g. In one preferred embodiment the centrifuging is for about 5 min. at about 300×g.

In one embodiment the method for selecting/obtaining a B-cell (clone) further comprises the following steps:
a) labeling the B-cells of a population of B-cells with (one to five) fluorescent dyes (optionally by incubating the B-cell population with two to five fluorescently labeled antibodies specifically binding to two to five different pre-determined B-cell surface markers),
b) optionally incubating the labelled cells in co-cultivation medium,
c) depositing those B-cells of the population of B-cells that have been labeled with at least one (one to five) fluorescent dye(s) (and optionally not labeled with the other fluorescent dye(s)) as single cells on EL-4 B5 feeder cells that have been irradiated with a dose of 9.5 Gy or less,
d) optionally centrifuging the single deposited B-cells/feeder cell mixture,
e) (individually) co-cultivating each single deposited B-cell with feeder the cells in a co-cultivation medium, which has been supplemented with a feeder mix,
f) selecting a B-cell clone proliferating and secreting an antibody in step e).

In one embodiment the method for producing an antibody specifically binding to a target further comprises the following steps
a) labeling the B-cells of a population of B-cells with (one to five) fluorescent dyes (optionally by incubating the B-cell population with two to five fluorescently labeled antibodies specifically binding to two to five different pre-determined B-cell surface markers),
b) optionally incubating the cells in co-cultivation medium,
c) depositing those B-cells of the population of B-cells that have been labeled with at least one (one to five) fluorescent dye(s) (and optionally not labeled with the other fluorescent dye(s)) as single cells EL-4 B5 feeder cells that have been irradiated with a dose of 9.5 Gy or less,
d) optionally centrifuging the single deposited B-cell/feeder cell mixture,
e) (individually) co-cultivating each single deposited B-cell with the feeder cells in a co-cultivation medium, which has been supplemented with a feeder mix,
f) selecting a B-cell clone of step e) secreting an antibody,
g) i) obtaining one or more nucleic acids encoding the secreted antibody's variable domains from the B-cell clone selected in step g),
   ii) if the B-cell clone is not a human B-cell clone humanizing the variable domains and providing the respective encoding nucleic acids, and
   iii) introducing the one or more nucleic acids in one or more expression vectors in frame with nucleic acid sequences encoding constant regions,
h) cultivating a cell (optionally selected from CHO and BHK cells), which has been transfected with the one or more expression vectors of step g), and recovering the antibody from the cell or the cultivation supernatant and thereby producing the antibody.

In one embodiment the method for producing an antibody further comprises the following steps
a) labeling the B-cells of a population of B-cells with (one to five) fluorescent dyes (optionally by incubating the B-cell population with two to five fluorescently labeled antibodies specifically binding to two to five different pre-determined B-cell surface markers),
b) optionally incubating the cells in co-cultivation medium,
c) depositing those B-cells of a population of B-cells that have been labeled with at least one (one to five) fluorescent dyes (and optionally not labeled with the other fluorescent dye(s)) as single cells on EL-4 B5 feeder cells that have been irradiated with a dose of 9.5 Gy or less,
d) optionally centrifuging the single deposited B-cell/feeder cell mixture,
e) (individually) co-cultivating each single deposited B-cell with the feeder cells in a co-cultivation medium, which has been supplemented with a feeder mix,
f) determining the binding specificity of the antibodies secreted in the cultivation medium of the co-cultivated B-cells for each supernatant individually,
g) selecting a B-cell clone of step 0 based on the binding properties of the secreted antibody,
h) obtaining one or more nucleic acids encoding the secreted antibody's variable domains from the B-cell clone selected in step g) by a reverse transcriptase PCR and nucleotide sequencing, (and thereby obtaining a monoclonal antibody variable light and heavy chain domain encoding nucleic acid,)
i) if the B-cell is a non-human B-cell humanizing the variable light and heavy chain domain and providing a nucleic acid encoding the humanized variable domains,
j) introducing the monoclonal antibody variable light and heavy chain variable domain encoding nucleic acid in one or more expression vectors (in frame with nucleic acids encoding antibody constant domains) for the expression of an (human or humanized) antibody,
k) introducing the expression vector(s) into a mammalian cell (optionally selected from CHO and BHK cells),
l) cultivating the cell and recovering the antibody from the cell or the cell culture supernatant and thereby producing the antibody.

In one embodiment the obtaining one or more nucleic acids encoding the secreted antibody's variable domains from the B-cell clone further comprises the following steps:
extracting total RNA from the antibody-producing B-cell clone,
performing a single stranded cDNA synthesis/reverse transcription of the extracted polyA$^+$ mRNA,
performing a PCR with a set of species specific primer,
optionally removal of the PCR primer/purification of the PCR product,
optionally sequencing of the PCR product.

In one embodiment the introducing the monoclonal antibody variable light and/or heavy chain variable domain encoding nucleic acid in an expression vector for the expression of an (human or humanized) antibody further comprises the following steps:
T4 polymerase incubation of the variable light and heavy chain variable domain,
linearization and amplification of the expression vector,
T4 polymerase incubation of the amplified expression vector,
sequence and ligation independent cloning of the variable domain encoding nucleic acid into the amplified expression vector, and
preparation of the vector(s) from pool of vector transformed *E. coli* cells.

In one embodiment of all aspects the method further comprises immediately prior to the labeling step the following step:

incubating the population of B-cells with (target) antigen, which is immobilized on a solid surface, and recovering (only) B-cells bound to the immobilized antigen.

In one embodiment of all aspects the population of B-cells is a non-human animal B-cell population. In one embodiment the B-cell population is a mouse B-cell population, or a hamster B-cell population, or a rabbit B-cell population, or a human immunoglobulin locus transgenic animal B-cell population. In one preferred embodiment the B-cell population is a rabbit B-cell population or a human immunoglobulin locus transgenic rabbit B-cell population.

In one embodiment of all aspects the population of B-cells is obtained from the blood of a non-human animal at least 4 days after the immunization. In one embodiment the population of B-cells is obtained from the blood of a non-human animal of from 4 days up to at most 13 days after immunization.

In one embodiment the B-cell population is a human B-cell population.

In one embodiment of all aspects the population of B-cells is obtained from blood by density gradient centrifugation.

In one embodiment of all aspects the B-cells are mature B-cells.

In one embodiment of all aspects the single cells are deposited (individually) into the wells of a multi-well plate.

In one embodiment of all aspects the feeder mix is natural thymocyte cultivation supernatant (TSN) or a defined and/or synthetic feeder mix. In one embodiment the thymocyte cultivation supernatant is obtained from thymocytes of the thymus gland of a young animal.

In one embodiment of all aspects the feeder mix is a defined and/or synthetic feeder mix. In one embodiment the defined and/or synthetic feeder mix comprises i) interleukin-1 beta and tumor necrosis factor alpha, and/or
ii) interleukin-2 (IL-2) and/or interleukin-10 (IL-10), and/or
iii) *Staphylococcus aureus* strain Cowan's cells (SAC), and/or
iv) interleukin-21 (IL-21) and optionally interleukin-2 (IL-2), and/or
v) B-cell activation factor of the tumor necrosis factor family (BAFF), and/or
vi) interleukin-6 (IL-6), and/or
vii) interleukin-4 (IL-4).

In one embodiment the feeder mix comprises IL-1B and TNF-α and one or more selected from IL-10, IL-21, SAC, BAFF, IL-2, IL-4, and IL-6.

In one embodiment the feeder mix comprises IL-1B, TNF-α, IL-10, SAC and IL-2.

In one embodiment of all aspects the B-cell population is a rabbit B-cell population and feeder mix is a thymocyte cultivation supernatant.

In one embodiment of all aspects the B-cell population is a rabbit B-cell population and the feeder mix is consisting of IL-1B, TNF-α, and any two of IL-2, IL-6 and IL-10.

In one embodiment of all aspects the B-cell population is a rabbit B-cell population and the feeder mix is consisting of IL-1B, TNF-α, IL-6 and IL-10.

In one embodiment of all aspects the B-cell population is a rabbit B-cell population and the feeder mix comprises IL-1B, TNF-α, IL-10, SAC and IL-2 or IL-6.

In one embodiment of all aspects the B-cell population is a rabbit B-cell population and the feeder mix comprises IL-1B, TNF-α, IL-21 and at least one of IL-2, IL-10 and IL-6.

In one embodiment of all aspects the B-cell population is a mouse B-cell population and the feeder mix comprises IL-1B, TNF-α and optionally one or more of BAFF, SAC, IL-21 and IL-6.

In one embodiment of all aspects the B-cell population is a mouse B-cell population and the feeder mix comprises IL-1B, IL-2, IL-10, TNF-α, BAFF and optionally IL-4.

In one embodiment of all aspects the B-cell population is a mouse B-cell population and the feeder mix comprises IL-1B, IL-2, IL-10, TNF-α and IL-6.

In one embodiment of all aspects the B-cell population is a hamster B-cell population and the feeder mix is consisting of IL-1B, TNF-α, and any one of IL-2, IL-6 and IL-10.

In one embodiment of all aspects the B-cell population is a hamster B-cell population and the feeder mix comprises IL-2 or IL-10 and IL-1B and TNF-α and optionally one or more of SAC, IL-21 and BAFF.

In one embodiment of all aspects the B-cell population is a hamster B-cell population and the feeder mix is consisting of IL-1B, TNF-α, IL-2, IL-6 and IL-10.

In one embodiment of all aspects the B-cell population is a hamster B-cell population and the feeder mix is consisting of IL-1B, TNF-α, IL-2, IL-6, IL-10 and SAC.

In one embodiment of all aspects the B-cell population is a hamster B-cell population and the feeder mix comprises IL-1B, TNF-α, IL-6, optionally SAC, at least one of IL-2 and IL-10 and optionally IL-4.

In one embodiment of all aspects the antibody is a monoclonal antibody.

In one embodiment of all aspects the labeling of the B-cells of the population of B-cells results in labeling of 0.1% to 2.5% of the cells of the (total) B-cell population.

In one embodiment of all aspects the labeling is of B-cell surface IgG.

In one preferred embodiment of all aspects the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of $IgG^+IgM^-$-B-cells).

In one embodiment of all aspects the incubation is with a fluorescently labeled anti-IgG antibody and a fluorescently labeled anti-light chain antibody (the labeling is of cell surface IgG and cell surface antibody light chain) and the selection is of cells positive for cell surface IgG and positive for cell surface antibody light chain (results in single cell deposition of IgG+LC+-B-cells).

In one embodiment of all previous embodiment the incubation is in addition with a fluorescently labeled anti-light chain antibody (the labeling is of cell surface antibody light chain in addition to the other two labels) and the selection is of cells positive for cell surface antibody light chain (results in single cell deposition of LC+-B-cells).

In one preferred embodiment of all aspects the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of $IgG^+IgM^-$-B-cells), whereby the population of B-cells has been incubated with (target) antigen, which is immobilized on a solid surface, and (only) B-cells bound to the immobilized antigen have been recovered and subjected to the incubation with the fluorescently labeled antibodies.

In one embodiment of all aspects the B-cell population is a rabbit B-cell population and the incubation is with a fluorescently labeled anti-IgG antibody (the labeling is of cell surface IgG) and the selection is of cells positive for cell surface IgG (results in single cell deposition of $IgG^+$-B-cells).

In one embodiment of all aspects the incubation of the rabbit B-cells is in addition with a fluorescently labeled anti-light chain antibody (the labeling is of cell surface antibody light chain in addition to the other two labels) and the selection is of cells positive for cell surface antibody light chain (results in single cell deposition of LC+-B-cells).

In one embodiment of all aspects the B-cell population is a rabbit B-cell population and the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of $IgG^+IgM^-$-B-cells).

In one preferred embodiment of all aspects the B-cell population is a rabbit B-cell population and the incubation is with a fluorescently labeled anti-IgG antibody, a fluorescently labeled anti-IgM antibody, and a fluorescently labeled anti-light chain antibody (the labeling is of cell surface IgG, cell surface IgM and cell surface light chain) and the selection is of cells positive for cell surface IgG and light chain and negative for cell surface IgM (results in single cell deposition of IgG+IgM--B-cells).

In one embodiment of all aspects the B-cell population is a murine B-cell population and the incubation is with a fluorescently labeled anti-IgG antibody (the labeling is of cell surface IgG) and the selection is of cells positive for cell surface IgG (results in single cell deposition of $IgG^+$-B-cells).

In one embodiment of all aspects the co-cultivating is in a co-cultivation medium comprising RPMI 1640 medium supplemented with 10% (v/v) FCS, 1% (w/v) of a 200 mM glutamine solution that comprises penicillin and streptomycin, 2% (v/v) of a 100 mM sodium pyruvate solution, and 1% (v/v) of a 1 M 2-(4-(2-hydroxyethyl)-1-piperazine)-ethane sulfonic acid (HEPES) buffer. In one embodiment the co-cultivation medium further comprises 0.05 mM beta-mercaptoethanol.

In one embodiment the animal is an experimental animal. In one embodiment the experimental animal is selected from mouse, hamster, and rabbit. In one embodiment the experimental animal is a rabbit.

DESCRIPTION OF THE FIGURES

FIG. 8A: The frequency (IgG-k wells in % of total wells) of IgG-secreting B-cell clones co-cultured with EL-4 B5 cells irradiated with 4 Gy or 50 Gy is shown.

FIG. 8B: The average IgG concentration (in µg/ml), i.e. the productivity, of IgG-secreting B-cell clones co-cultured with EL-4 B5 cells irradiated with 4 Gy or 50 Gy is shown.

The medium was supplemented with 1.25 vol-%, 2.5 vol-%, or 5 vol-% TSN, respectively. The average with SD of three 96-well plates is shown.

Figure 9:
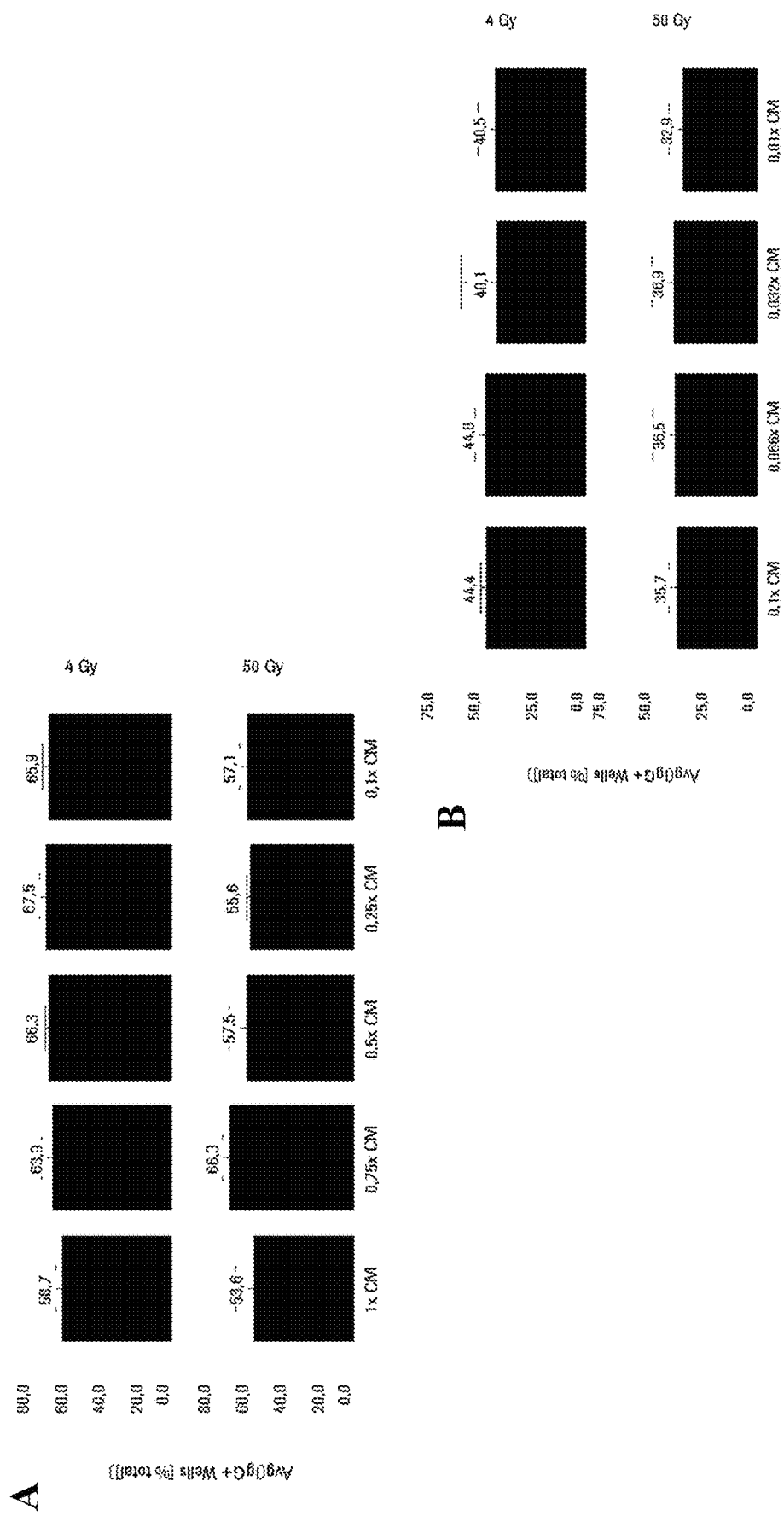

FIG. 9 Interrelation of the irradiation dose of the feeder cells and the cytokine concentrations on the frequency of rbIgG+ wells in % of total wells after co-culture of single deposited B-cells with EL-4 B5 cells.

FIG. 9A: Data with 20 k EL-4 B5 cells irradiated with 4 Gy per well. The medium was supplemented with concentration fractions of a cytokine mix (CM) from 1× to 0.1× (Experiment 1, upper bar diagram) and from 0.1× to 0.01× (Experiment 2, lower bar diagram). The average with SD of three 96-well plates is shown.

FIG. 9B: data with 50 k EL-4 B5 cells irradiated with 50 Gy per well. The medium was supplemented with concentration fractions of a cytokine mix (CM) from 1× to 0.1× (Experiment 1, upper bar diagram) and from 0.1× to 0.01× (Experiment 2, lower bar diagram). The average with SD of three 96-well plates is shown.

Figure 10:
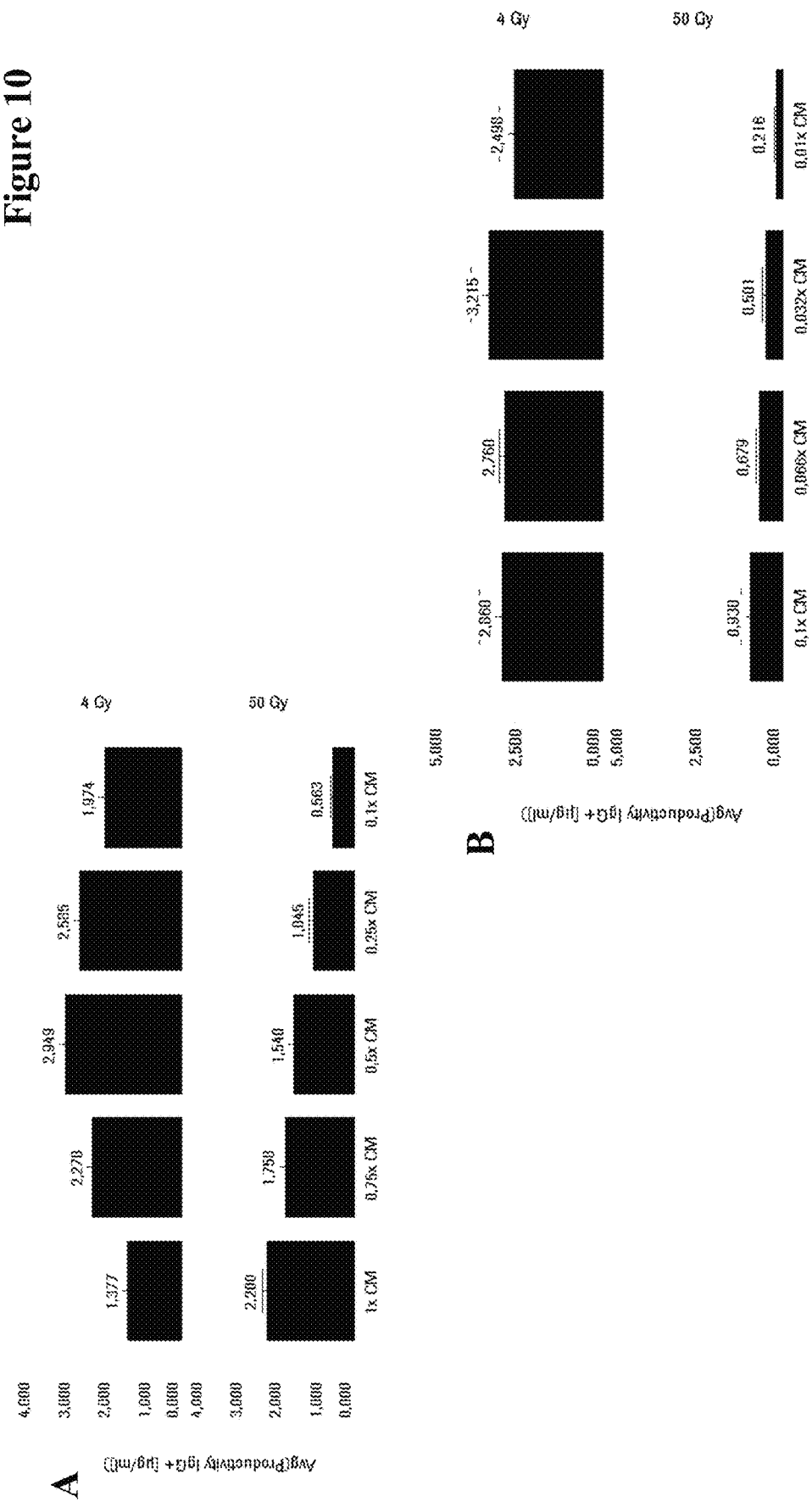

FIG. 10 Interrelation of the irradiation dose of the feeder cells and the cytokine concentrations on the average IgG concentration of B-cell clones, i.e. productivity, in rbIgG+ wells after co-culture of single deposited B-cells with EL-4 B5 cells.

FIG. 10A: EL-4 B5 cells irradiated with 4 Gy (20 k/well). The medium was supplemented with concentration fractions of a diagram) and from 0.1× to 0.01× (Experiment 2, lower bar diagram). The average with SD of three 96-well plates is shown.

FIG. 10B: EL-4 B5 cells irradiated with 50 Gy (50 k/well). The medium was supplemented with concentration fractions of a cytokine mix (CM) from 1× to 0.1× (Experiment 1, upper bar diagram) and from 0.1× to 0.01× (Experiment 2, lower bar diagram). The average with SD of three 96-well plates is shown.

DEFINITIONS

The term "Gray" or short "Gy" denotes a commonly used unit of ionizing radiation dose. It is defined as the absorption of one joule of radiation energy per kilogram of matter, in the current case cells (wet cell weight). Thereby the absorbed dose can be measured. This unit is purely physical and does not depend or take into account biological parameters, i.e. the "Gray" is defined independently of the material for which it is given. For conversion the rad unit used in the United States the following conversion factor can be used: 1 rad=0.01 Gy.

"Affinity" refers to the strength of the total sum of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (kd). Affinity can be measured by common methods known in the art, including those described herein. Specific illustrative and exemplary embodiments for measuring binding affinity are described in the following.

The term "antibody" herein is used to denote naturally occurring antibodies including their naturally occurring structural variants.

For example, native (human, mouse, rat, rabbit) IgG antibodies are heterotetrameric glycoproteins with a molecular weight of about 150,000 Dalton. Native IgG antibodies are composed of two identical light chains and two identical heavy chains comprising inter- and intra-chain disulfide bonds, so that all four chains are covalently linked to each other. From N- to C-terminus, each heavy chain has a variable region (VH), also called a variable heavy chain domain or a heavy chain variable domain, followed by three constant domains (CH1, CH2, and CH3), whereby a flexible hinge region is located between the first and the second constant domain. The heavy chain of an antibody may be assigned to one of five types, called IgA, IgD, IgE, IgG and IgM, depending on their sequence and domain structure ("class" of an antibody). Several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. Similarly, from N- to C-terminus, each light chain has a variable region (VL), also called a variable light chain domain or a light chain variable domain, followed by a constant light chain domain (CL). The light chain of an antibody may be assigned to one of two types, called kappa (κ) and lambda (λ), based on the amino acid sequence of its constant domain.

For example, native (camelid, i.e. from Camelidae, sub-order Tylopoda, which includes camels, dromedaries and llamas) heavy-chain only antibodies (VHH antibodies) do not comprise a classical CH1 domain as found in conventional IgG heavy chains, and, thus, are expressed as VHH domains fused directly to the hinge-CH2-CH3 domains of an antibody. The variable region sequences from llama derived VHH antibodies, for example, are similar to sequences in the human VH3 family of variable domains (Schroeder et al., Int. Immunol. 2 (1989) 41-50). Compared to antibodies of the IgG type the CDR3 domain amino acid sequence in L. llama VHH domains is longer on average than most CDR3 domains of classical IgG type antibodies comprising heavy and light chains. Alike classical IgG antibodies the position of the CDRs in VHH antibodies can be determined by methods well known in the art (see e.g. U.S. Pat. No. 5,637,677). Residues 11, 37, 44, 45 and 47 are important for the formation of the chain interface (see e.g. WO 99/42077).

An "antibody fragment" refers to a molecule other than an intact antibody (IgG/VHH=four chain/two chain) comprising only a portion of an intact antibody and that binds to the same antigen to which the intact antibody binds. Examples of antibody fragments include but are not limited to Fv, Fab, Fab', Fab'-SH, F(ab')₂; diabodies; linear antibodies; single-chain antibody molecules (e.g. scFv); single domain antibodies; and multispecific antibodies formed from antibody fragments.

The term "cell" includes both prokaryotic cells, which are used for propagation of plasmids, and eukaryotic cells, which are used for the expression of a nucleic acid. In one embodiment the eukaryotic cell is a mammalian cell. In one embodiment the mammalian cell is a CHO cell, optionally a CHO K1 cell (e.g. a ATCC CCL-61 or DSM ACC 110), or a CHO DG44 cell (also known as CHO-DHFR[-], e.g. a DSM ACC 126), or a CHO XL99 cell, a CHO-T cell (see e.g. Morgan, D., et al., Biochemistry 26 (1987) 2959-2963), or a CHO-S cell, or a Super-CHO cell (Pak, S. C. O., et al. Cytotechnol. 22 (1996) 139-146), or BHK cell, or a NS0 cell, or a Sp2/0 cell, or a HEK 293 cell, or a HEK 293 EBNA cell, or a PER.C6® cell, or a COS cell. If these cells are not adapted to growth in serum-free medium or in suspension an adaptation prior to the use in the current method can be performed. As used herein, the expression "cell" includes the subject cell and its progeny. Thus, the words "transformant" and "transformed cell" include the primary subject cell and cultures derived there from without regard for the number of transfers or sub-cultivations. It is also understood that all progeny may not be precisely identical in DNA content, due to deliberate or inadvertent mutations. Variant progeny that have the same function or biological activity as screened for in the originally transformed cell are included.

The term "clone" denotes a population of dividing and antibody secreting B-cells arising from/originating from a single B-cell. Thus, a B-cell clone is a homogeneous population of B-cells and produces a monoclonal antibody.

The term "cognate pair of antibody variable domains" denotes a pair of antibody variable domains that is obtained from a single antibody secreting B-cell (clone), i.e. which has been generated as pair during the immune response of a mammal due to the contact with an immunogenic molecule or which have been assembled randomly during a display approach.

The term "experimental animal" denotes a non-human animal. In one embodiment the experimental animal is selected from rat, mouse, hamster, rabbit, camel, llama, non-human primates, sheep, dog, cow, chicken, amphibians, sharks and reptiles. In one embodiment the experimental animal is a rabbit.

The term "expression" as used herein refers to transcription and/or translation and secretion processes occurring within a cell. The level of transcription of a nucleic acid sequence of interest in a cell can be determined on the basis of the amount of corresponding mRNA that is present in the cell. For example, mRNA transcribed from a sequence of interest can be quantified by qPCR or RT-PCR or by Northern hybridization (see Sambrook, et al., Molecular Cloning: A Laboratory Manual, Second Edition, Cold Spring Harbor Laboratory Press, Cold Spring Harbor, N.Y. (1989)). Polypeptides encoded by a nucleic acid can be quantified by various methods, e.g. by ELISA, by assaying the biological activity of the polypeptide, or by employing assays that are independent of such activity, such as Western blotting or radioimmunoassay, using immunoglobulins that recognize and bind to the polypeptide (see Sambrook, et al., (1989), supra).

To a person skilled in the art procedures and methods are well known to convert an amino acid sequence, e.g. of a polypeptide, into a corresponding nucleic acid sequence encoding this amino acid sequence and vice versa. Therefore, a nucleic acid is characterized by its nucleic acid sequence consisting of individual nucleotides and likewise by the amino acid sequence of a polypeptide encoded thereby.

Antibodies are in general secreted into the cultivation medium by the cell producing it.

The term "feeder mix" denotes a combination of different additives, such as growth factors, cytokines and/or further proteins promoting the activation and/or survival of B-cells and/or antibody secretion. The feeder mix can be a natural feeder mix, e.g. obtained from the cultivation supernatant of thymocytes (TSN), which is a non-defined combination of cytokines. Alternatively, the feeder mix can be a defined and/or synthetic feeder mix, which is a defined combination of different recombinantly produced or chemically synthesized additives, such as growth factors, cytokines and/or further proteins promoting the activation and/or survival of B-cells and/or antibody secretion.

The terms "host cell", "host cell line", and "host cell culture" are used interchangeably and refer to cells into which exogenous nucleic acid has been introduced, including the progeny of such cells. Host cells include "transformants" or "transfectants" and "transformed cells" and "transfected cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is an antibody, which possesses an amino acid sequence that corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

An "individual" or "subject" is a vertebrate. In one embodiment the vertebrate is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human. In other embodiments the individual or subject is a rabbit.

The term "labeling" denotes a process for determining the presence or absence of a surface marker, which can be determined by binding/non-binding of a specifically binding and labeled anti-surface marker antibody to a cell. Thus, the presence of a surface marker is determined e.g. in the case of a fluorescence label by the occurrence of a fluorescence whereas the absence of a surface marker is determined by the absence of a fluorescence after incubation of a cell or a population of cells with the respective specifically binding and labeled anti-surface marker antibody.

The term "monoclonal antibody" as used herein refers to an antibody obtained from a population of substantially homogeneous antibodies produced by a single cell clone, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to methods utilizing transgenic animals containing all or part of the human immunoglobulin loci, such methods and other exemplary methods for making monoclonal antibodies being described herein.

The term "PMA" denotes phorbol-12-myristate-13-acetate, a small chemical compound. The IPUAC name thereof is (1aR,1bS,4aR,7aS,7bS,8R,9R,9aS)-9a-(acetyloxy)-4a, 7b-dihydroxy-3-(hydroxymethyl)-1,1,6,8-tetramethyl-5-oxo-1 a,1b,4,4a,5,7a,7b,8,9,9a-decahydro-H-cyclopropa[3, 4]benzo[1,2-e]azulen-9-yl myristate. This compound is also denoted as TPA, 12-O-tetradecanoylphorbol-13-acetate, tetradecanoylphorbol acetate, tetradecanoyl phorbol acetate, phorbol myristate acetate, 12-O-tetradecanoylphorbol 13-acetate, 12-tetradecanoylphorbol 13-acetate, 12-tetradecanoylphorbol 13-monoacetate, 13-O-acetylphorbol 12-myristate, 4β-phorbol 12-myristate 13-acetate, myristic acid, 9-ester with 1,1aα,1bβ,4,4a,7aα,7b,8,9,9a-decahydro-4aβ, 7bα,9β,9aα-tetrahydroxy-3-(hydroxymethyl)-1,1,6, 8α-tetramethyl-5H-cyclopropa[3,4]benz[1,2-e]azulen-5-one 9a-acetate, (+)-, phorbol 12-myristate 13-acetate, phorbol 12-tetradecanoate 13-acetate, phorbol myristate acetate, PMA, PMA (tumor promoter), tetradecanoic acid, (1aR,1 bS,4aR,7aS,7bS,8R,9R,9aS)-9a-(acetyloxy)-1a,1b,4, 4a,5,7a,7b,8,9,9a-decahydro-4a,7bdihydroxy-3-(hydroxymethyl)-1,1,6,8-tetramethyl-5-oxo-1H-cyclopropa[3,4]benz [1,2-e]azulen-9-yl ester, tetradecanoic acid, 9a-(acetyl oxy)-1a,1b,4,4a,5,7a,7b, 8,9,9a-decahydro-4a,7b-dihydroxy-3-(hydroxymethyl)-1,1,6,8-tetramethyl-5-oxo-1H-cyclopropa [3,4]benz[1,2-e]azulen-9-yl ester, [1aR(1aα,1bβ,4aβ,7aα, 7bα,8α,9β,9aα)]-, TPA and TPA (phorbol derivative).

The term "specifically binding" and grammatical equivalents thereof denote that the antibody binds to its target with a dissociation constant (KD) of $10^{-7}$M or less, in one embodiment of from $10^{-8}$ M to $10^{-13}$ M, in a further embodiment of from $10^{-9}$ M to $10^{-13}$ M. The term is further used to indicate that the antibody does not specifically bind to other biomolecules present, i.e. it binds to other biomolecules with a dissociation constant (KD) of $10^{-6}$M or more, in one embodiment of from $10^{-6}$M to 1 M.

The term "variable region" or "variable domain" refers to the region of an antibody heavy or light chain that is involved in the binding of the antibody to its antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J., et al., Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

DETAILED DESCRIPTION OF EMBODIMENTS OF THE INVENTION

The current invention is based at least in part on the finding that EL-4 B5 cells irradiated with a dose of 9.5 Gy or less of gamma irradiation have advantageous properties when used in a B-cell co-cultivation (BCC) method.

I. General Aspects

Immunization

For the generation of therapeutic antibodies either a non-human animal is immunized with the therapeutic target (either alone or in combination with an immunogenic stimulus) to elicit an immune response or synthetic approaches, such as phage display libraries are used. If a transgenic animal (i.e. having a human immune system) or a human phage display library is used human antibodies are obtained. Otherwise non-human animal antibodies are obtained that will be humanized thereafter. A rare possibility to obtain potential therapeutic antibodies is from the blood of a human being that has recovered from a disease.

Often non-human animals, such as mice, rabbits, hamster and rats, are used as animal model for evaluating antibody based therapies. Therefore, it is normally required to provide cross-reactive antibodies binding to the non-human animal antigen as well as to the human antigen.

In the method as reported herein B-cells obtained from any source e.g. human, mouse, hamster or rabbit, can be used. Depending on the source of the B-cell the feeder cells and the feeder mix are adjusted/chosen.

In one embodiment the rabbit is selected from New Zealand White (NZW) rabbits, Zimmermann-rabbits (ZIKA), Alicia-mutant strain rabbits, basilea mutant strain rabbits, transgenic rabbits with a human immunoglobulin locus, rbIgM knock-out rabbits, and cross-breeding thereof.

In one embodiment the hamster is selected from Armenian hamster (*Cricetulus migratorius*), Chinese hamster (*Cricetulus griseus*), and Syrian hamster (*Mesocricetulus auratus*). In a preferred embodiment the hamster is the Armenia hamster.

Source and Isolation of B-Cells

The blood provides a high diversity of antibody producing B-cells. The therefrom obtained B-cell clones secrete antibodies showing a high diversity.

In one embodiment B-cells, e.g. from the blood, are obtained of from 4 days after immunization until at most 13 days after immunization or the most recent boost of the non-human animal. This time span allows for a high flexibility in the method as reported herein. In this time span it is likely that the B-cells providing for the most affine antibodies migrate from spleen to blood (see e.g. Paus, D., et al., JEM 203 (2006) 1081-1091; Smith, K. G. S., et al., The EMBO J. 16 (1997) 2996-3006; Wrammert, J., et al., Nature 453 (2008) 667-672).

B-cells from the blood, e.g. of a non-human animal or from human blood, may be obtained with any method known in the art. For example, density gradient centrifugation (DGC) or red blood cell lysis (lysis) can be used. Density gradient centrifugation compared to hypotonic lysis provides for a higher overall yield, i.e. number of B-cell clones. Additionally, from the cells obtained by density gradient centrifugation a larger number of cells divides and grows in the co-cultivation step. Also the concentration of secreted antibody is higher compared to cells obtained with a different method. Therefore, in one embodiment the providing of a population of B-cells is by density gradient centrifugation. Alternative methods can likewise be used for the isolation of B-cells.

Selection Steps Prior to Co-Cultivation

B-cells producing antibodies that specifically bind an antigen can be enriched from peripheral blood mononuclear cells (PBMCs). Thus, in one embodiment of all methods as reported herein the B-cell population is enriched from peripheral blood mononuclear cells (PBMCs).

In one embodiment of all methods as reported herein the PBMCs are depleted of macrophages. This is advantageous for B-cells of rabbit origin for the co-cultivation step.

Macrophages can be depleted from PBMCs by adhesion to the surface of the cell culture plate (see pre-incubation step).

Incubating the population of B-cells in co-cultivation medium prior to the single cell depositing increases the total number of antibody secreting cells obtained after the single cell depositing compared to a single cell depositing directly after the isolation and optional enrichment of the population of B-cells from the blood of a non-human animal (in one embodiment the non-human animal is a rabbit). Specifically, the incubating is at about 37° C. for about one hour in EL-4 B5 medium, e.g. using a cell culture incubator.

In one embodiment of the methods as reported herein the cells are from a protein-immunized animal and are depleted of macrophages prior to the labeling.

Cells not producing an antibody binding the antigen or, likewise, cells producing an antibody binding to the antigen can be reduced or enriched, respectively, by using a panning approach. Therein the respective antigen is presented attached to a surface and cells binding thereto are selectively enriched in the cell population in case the bound cells are processed further, or reduced in the cell population in case the cells remaining in solution are processed further.

The method as reported herein comprises in one embodiment prior to the single cell depositing a selecting step in which B-cells producing specific and/or non-cross-reactive antibodies are selected based on cell surface markers and fluorescence activated cell sorting/gating. In one embodiment mature B-cells are sorted/enriched/selected. For selection of B-cells from different non-human animal species different cell surface markers can be used.

With the labeling of non-target cell populations and non-specifically binding lymphocytes it is possible to selectively deplete these cells. In this depletion step only a partial depletion can be achieved. Albeit the depletion is not quantitative it provides for an advantage in the succeeding fluorescence labeling of the remaining cells as the number of interfering cells can be reduced or even minimized. By a single cell depositing of mature B-cells (memory B-cells, affinity matured plasmablasts and plasma cells) by fluorescence activated cell sorting using the labeling a higher number of IgG$^+$-wells/cell clones can be obtained in the co-cultivation step.

Different cell populations can be labeled by using different surface markers such as CD3$^+$-cells (T-cells), CD19$^+$-cells (B-cells), IgM$^+$-cells (mature naive B-cells), IgG$^+$-cells (mature B-cells), CD38$^+$-cells and CD138 cells (e.g. plasmablasts), and IgG$^+$CD38$^+$CD27$^+$-cells (pre-plasma cells).

Immuno-fluorescence labeling for selection of mature IgG$^+$-B-cells, such as memory B-cells, plasmablasts, and plasma cells, is available. For a selection or enrichment of B-cells the cells are either single labeled, or double labeled, or triple labeled. Also required is a labeling that results in about 0.1% to 2.5% of labeled cells of the total cell population.

In one embodiment B-cells are deposited as single cells selected by the labeling of surface molecules present on 0.1% to 2.5% of the B-cells in the population, in another embodiment on 0.3% to 1.5% of the B-cells of the population, in a further embodiment on 0.5% to 1% of the B-cells of the population.

The labeling of $CD27^+CD138^+$-cells or $CD3^-CD27^+$-cells results in about 1.5% of the cells of the cell population to be labeled, respectively.

Of $IgG^+$-B-cells within the PBMC population 0.5-1% can be doubly labeled as $IgG^+CD19^+$-cells, $IgG^+CD38^+$-cells, and $IgG^+CD268^+$-cells.

Of $IgG^-$-B-cells within the PBMC population 0.5-1% can be doubly labeled as $IgG^-CD138^+$-cells.

Of $IgG^+$-hamster-B-cells within the PBMC population 0.6%±0.1% can be doubly labeled as $IgG^+IgM^-$-hamster-B-cells.

In one embodiment of all methods as reported herein $IgG^+CD19^+$-B-cells are deposited as single cells from the B-cells obtained from a non-immunized non-human animal or human.

The deposition of $IgG^+CD19^+$-murine-B-cells as single cells results in an improved number of $IgG^+$-wells in the succeeding co-cultivation step.

The deposition of $IgG^-CD138^+$-murine-B-cells as single cells results in cells producing the highest number of B-cell clones and the highest concentration of IgG.

In one embodiment the method is with the proviso that if the cells are of rabbit origin the labeling is not of $IgG^+$-B-cells and/or $CD138^+$-B-cells.

Table: Exemplary immunofluorescence labeling for the determination of mature mouse-, hamster- and rabbit-B-cells.

| B-cell origin | sorting of B-cells with | fraction of all viable cells (%) |
|---|---|---|
| mouse | $IgG^+CD19^+$ | 0.5 ± 0.2 n = 14 |
| mouse | $IgG^+CD38^+$ | 0.8 ± 0.5 n = 9 |
| mouse | $IgG^+CD138^+$ | 0.06 ± 0.07 n = 6 |
| mouse | $IgG^-CD138^+$ | 0.6 ± 0.5 n = 6 |
| mouse | $IgG^+CD27^+$ | 0.1 ± 0.1 n = 8 |
| mouse | $CD27^+CD138^+$ | 1.5 ± 0.5 n = 2 |
| mouse | $CD27^+IgG^+CD3^-$ | 0.10 ± 0.04 n = 3 |
| mouse | $CD3^-CD27^+$ | 1.33 n = 1 |
| mouse | $IgG^+CD268^+$ | 0.8 n = 1 |
| mouse | $CD38^+CD3^-$ | 12 ± 7 n = 2 |
| hamster | $IgG^+IgM^-$ | 0.6 ± 0.1 n = 15 |
| rabbit | $IgG^+$ | 0.6 ± 0.2, n = 5 |
| rabbit | $IgG^+IgM^-$ | 0.4 ± 0.2, n = 2 |
| rabbit | $IgG^+CD138^+$ | 0.3 ± 0.1, n = 5 |

In one embodiment the methods comprise the step of depleting the B-cell population of macrophages and enriching of B-cells of the B-cell population secreting antibody specifically binding a target antigen.

Single Cell Depositing

The method as reported herein comprises the step of depositing the B-cells of a B-cell population as single cells. In one embodiment of all methods as reported herein the depositing as single cells is by fluorescence activated cell sorting (FACS). The surface marker used for the labeling required for the FACS single cell depositing can be with the specific marker combination as outlined herein.

An additional centrifugation step after the single cell depositing and prior to the co-cultivation increases the number of antibody secreting cells and increases the amount of the secreted IgG.

In one embodiment of all methods as reported herein the method comprises the step of centrifuging the single deposited cells prior to the co-cultivation. In one preferred embodiment the centrifuging is for 5 min. at 300×g.

Co-Cultivation

The single deposited B-cells are co-cultivated with feeder cells in the presence of a feeder mix. In one embodiment the B-cells are co-cultivated with murine EL-4 B5 cells as feeder cells.

As outlined above an increase in the yield in the co-cultivation step (number of $IgG^+$-wells/cell clones as well as IgG-concentration) and also an enrichment or isolation of mature $IgG^+$-B-cell from PBMCs can be achieved by suitable immuno fluorescence labeling.

Depositing $IgG^+CD19^+$- and/or $IgG^+CD38^+$-B-cells from freshly isolated PBMCs as single cells results in the highest number of $IgG^+$-wells/cell clones can be obtained.

Depositing $IgG^+CD19^+$-, $IgG^+CD38^+$- and/or $IgG^-CD138^+$-B-cells as single cells after the depletion of macrophages or KLH-specific cells (keyhole limpet haemocyanine) good results can be obtained.

Depositing $IgG^+CD19^+$-, $IgG^+CD38^+$- and/or $IgG^-CD138^+$-B-cells as single cells after the depletion of antigen-specific B-cells improved results can be obtained.

A deposition as single cells based on a labeling as outlined above results in the highest fraction of $IgG^+$-wells/cell clones and in the wells/cell clones with the highest IgG-concentration in the supernatant.

For murine B-cells with the single cell depositing of $IgG^+CD19^+$-cells after each enrichment and/or depletion step the highest number of $IgG^+$-wells/cell clones after co-cultivation can be obtained. Alternatively, with the single cell depositing of $IgG^-CD138^+$-cells wells/cell clones with the best IgG-concentration in the supernatant can be obtained. The single cell depositing of $IgG^-CD138^+$-cells can be used for B-cells from immunized non-human animals. The single cell depositing of $IgG^+CD19^+$-cells can be used for B-cells from non-immunized non-human animals.

The single cell depositing of $IgG^+IgM^-$-cells can be used for hamster-B-cells of immunized and non-immunized non-human animals.

The single cell depositing of $IgG^+$, and/or $IgG^+CD138^+$-, and/or $CD138^+$- and/or $IgG^+IgM^-$-B-cells can be used for rabbit B-cells.

The immuno-fluorescence labeling used for B-cells obtained from the blood of an experimental non-human animal can also be used for the labeling of B-cells obtained from the spleen and other immunological organs of an experimental non-human animal, such as, e.g., mouse, hamster and rabbit. For mouse B-cells the fraction of $IgG^+$-B-cells from spleen was about 0.8% compared to 0.4% for $IgG^+CD19^+$-cells. For hamster B-cells the respective numbers are 1.9% and 0.5% $IgG^+IgM^-$-cells. For rabbit-blood derived B-cells 0.2% of $IgG^+$-cells were found after depletion of macrophages. Peyer'sche plaques from rabbit showed 0.4% of $IgG^+$-cells and spleen showed 0.3% of $IgG^+$-cells after depletion of macrophages.

With the methods as reported herein after about seven (7) days, i.e. after 5, 6, 7, or 8 days, especially after 7 or 8 days, of co-cultivation antibody concentrations of from about 30 ng/ml up to 15 µg/ml or more can be obtained (average value about 500 ng/ml). With the thereby provided amount of antibody a high number of different analyses can be performed in order to characterize the antibody, e.g. regarding binding specificity, in more detail. With the improved characterization of the antibody at this early stage in the screening/selection process it is possible to reduce the number of required nucleic acid isolations and sequencing reactions that have to be performed. Additionally, the B-cell clone provides an amount of mRNA encoding monoclonal light and heavy chain variable region allowing the use of degenerated PCR primer and obviates the requirement of highly specific primer. Also the required number of PCR cycles is reduced. Thus, in one embodiment the reverse transcriptase PCR is with degenerated PCR primer for the light and heavy chain variable domain.

The co-cultivation step with feeder cells can be preceded and also succeeded by a number of additional steps.

In one embodiment of all methods as reported herein the feeder mix is a thymocyte cultivation supernatant. In a specific embodiment the thymocyte cultivation supernatant is obtained from the thymocytes of the thymus gland of the respective young non-human animal. It is especially suited to use the thymus gland of young non-human animals compared to the isolation of thymocytes from the blood adult non-human animals. The term "young non-human animal" denotes a non-human animal before sexual maturity occurs. A young hamster, for example, is of an age of less than 6 weeks, especially less than 4 weeks. A young mouse, for example, is of an age of less than 8 weeks, especially less than 5 weeks.

Due to the origin of the feeder mix, which is derived from the supernatant of cultivated thymocytes (thymocyte cultivation supernatant—TSN), considerable batch to batch variations occur.

In order to overcome this variability a defined (and synthetic) feeder mix consisting of defined (synthetic) components can be employed.

A defined (synthetic) feeder mix consisting of IL-1β (interleukin-1 beta), TNF-α (tumor necrosis factor alpha), IL-2 (interleukin-2) and IL-10 (interleukin-10) is known from Tucci, A., et al., J. Immunol. 148 (1992) 2778-2784.

The B-cell-species-specific additives for the defined (synthetic) feeder mix result in increased amounts of secreted antibody by the respective B-cell clone. Concomitantly highly producing cells contain more mRNA which in turn facilitates the reverse transcription and sequencing of the encoding nucleic acid, e.g. with a redundant, non-specific primer set.

By the addition of SAC (*Staphylococcus aureus* strain Cowan's cells, a single SAC lot was used) the number of antibody secreting B-cells and the average IgG-concentration in the supernatant after co-cultivation can be increased. For the addition of SAC in the co-cultivation a concentration range can be defined as reduced as well as increased concentrations of SAC reduce the amount of secreted antibody.

A SAC ratio of from 1:20000 to 1:150000 provides for an increased number of IgG+-wells/cell clones, whereby the ratio of from 1:50000 to 1:100000 shows the highest numbers. In one embodiment the amount of SAC added to the cultivation medium is determined by providing a dilution series and determining the dilution at which the added SAC provides for the highest number of IgG positive wells/cell clones.

By the addition of SAC to the feeder-mix the co-cultivation of B-cells is changed in such a way that only single deposited B-cells have a benefit in growth, whereas B-cell growth was inhibited when using a PBL (e.g. B-cells and endogenous T cells) mixture for co-cultivation.

In one embodiment of all methods as reported herein the defined (synthetic) feeder mix for the co-cultivation of murine B-cells comprises IL-1β, IL-2, IL-10, TNF-α and BAFF. In one embodiment BAFF is added at a concentration of 5 ng/ml.

In one embodiment of all methods as reported herein the defined (synthetic) feeder mix for the co-cultivation of hamster B-cells comprises IL-1β, IL-2, IL-10, TNF-α, IL-6 and SAC. In one embodiment IL-6 is added at a concentration of 10 ng/ml. In one embodiment SAC is added at a 1:75,000 ratio.

A co-cultivation of feeder cells and murine B-cells without IL-2, without IL-10, as well as without IL-2 and IL-10 results in an increase in the yield of IgG+-wells albeit the IgG-concentration is reduced. Without TNFα the IgG-concentration is also reduced. Without IL-1β no IgG can be found in the supernatant.

A co-cultivation of hamster B-cells without IL-2 or without IL-10, respectively, results in IgG+-wells with detectable IgG-concentration. In contrast thereto in a co-cultivation without IL-2 and IL-10 almost no B-cell growth can be detected. In the absence of TNF-α or IL-1β no IgG-secretion can be determined.

In the presence of EL-4 B5 feeder cells at least IL-1β and TNFα are required for the co-cultivation of mouse, hamster and rabbit B-cells. IL-2 and IL-10 can be omitted for the co-cultivation of murine cells. Hamster B-cells can be cultivated in the absence of either IL-2 or IL-10. Rabbit B-cells can be cultivated in the absence of either IL-2 or IL-10 or IL-6.

For murine and hamster B-cells the addition of IL-4 to the feeder mix increases the number of IgG+-wells/cell clones as well as the IgG-concentration in the supernatant. Thus, in one embodiment of all methods as reported herein the feeder mix for the co-cultivation of murine- or hamster-B-cells comprises IL-4.

The addition of IL-6 to the feeder mix for the co-cultivation of murine-B-cells or hamster-B-cells results in an increased number of IgG+-wells/cell clones or increased IgG-concentration, respectively. Thus, in one embodiment of all methods as reported herein the feeder mix for the co-cultivation of murine-B-cells or hamster-B-cells comprises IL-6. In one embodiment the IL-6 is added at a concentration of 50 ng/ml. In one embodiment IL-6 is added at a concentration of 10 ng/ml, if high IgG-concentration is required. In one embodiment the addition of IL-6 is after three days of co-cultivation of the selected B-cells and EL-4 B5 cells.

In one embodiment IL-1β, TNF-α, IL-2, IL-10 and IL-21 are recombinant murine IL-1β, murine TNF-α, murine IL-2, murine IL-10, and murine IL-21.

In one embodiment BAFF is added at a concentration of 5 ng/ml.

In one embodiment IL-6 is added at a concentration of 10 ng/ml.

In one embodiment SAC is added at a 1:75,000 ratio.

In one embodiment and feeder cells are murine EL-4 B5 cells.

The addition of an inhibitor of a certain potassium channel (=PAP-1, 5-(4-phenoxy butoxy) psoralene) increases the rbIgG secretion of B-cells in a concentration dependent manner without decreasing the number of B-cell clones. Usually a cytokine which induced rbIgG productivity can be correlated with a decrease of the overall number of B-cell clones. This was not the case with PAP-1.

With a TSN concentration of 7.5% the highest IgG concentration in the supernatant can be obtained.

The co-cultivation is in one embodiment of all methods as reported herein in polystyrene multi well plates with wells with a round bottom. The working volume of the wells is in one embodiment of all methods as reported herein of 50 μl to 250 μl. In one embodiment the wells are coated at least partially with a non-fibrous substrate prepared from a blend of polymer plastic resin and amphipathic molecules, wherein the amphipathic molecule comprises a hydrophilic moiety and a hydrophobic region, wherein the hydrophobic regions are anchored within the substrate and the hydrophilic moieties are exposed on the substrate. In one embodiment the amphipathic molecules are chosen from alkylamine ethoxylated, poly (ethylene imine), octyldecamine or mixtures thereof (see e.g. EP 1 860 181).

Characterization of Co-Cultivated Cells

For the (qualitative and quantitative) determination of secreted IgG after the co-cultivation generally all methods known to a person of skill in the art such as an ELISA can be used. In one embodiment of all methods as reported herein an ELISA is used.

Depending on the characterization results a B-cell clone can be obtained, i.e. selected. The term "clone" denotes a population of dividing and antibody secreting B-cells arising from/originating from a single B-cell. Thus, a B-cell clone produces a monoclonal antibody.

Isolation of mRNA, Cloning and Sequencing

From the B-cells the total mRNA can be isolated and transcribed in cDNA. With specific primers the cognate VH- and VL-region encoding nucleic acid can be amplified. Almost no identical sequences are obtained. The method provides for highly diverse antibodies binding to the same antigen.

The primers used for the amplification of the VH-encoding nucleic acid can be used for cDNA obtained from cells from the NMRI-mouse, the Armenian Hamster, the Balb/c-mouse as well as the Syrian hamster and the rabbit.

In one embodiment of all methods as reported herein the amino acid sequence is derived from the amplified VH-encoding nucleic acid and the exact start and end point is identified by locating the amino acid sequences of EVQL/QVQL to VSS (VH-region) and DIVM/DIQM to KLEIK (VL-region).

Also reported herein is a method for producing an antibody comprising the following steps:
a) providing a population of (mature) B-cells (obtained from the blood of an experimental non-human animal),
b) staining the cells of the population of B-cells with at least one fluorescence dye (in one embodiment with one to three, or two to three fluorescence dyes),
c) depositing single cells of the stained population of B-cells in individual containers (in one embodiment is the container a well of a multi well plate),
d) cultivating the deposited individual B-cells in the presence of feeder cells and a feeder mix (in one embodiment the feeder cells are EL-4 B5 cells, in one embodiment the feeder mix is natural TSN, in one embodiment the feeder mix is a defined (and/or synthetic) feeder mix,
e) determining the binding specificity of the antibodies secreted in the cultivation of the individual B-cells,
f) determining the amino acid sequence of the variable light and heavy chain domain of specifically binding antibodies by a reverse transcriptase PCR and nucleotide sequencing, and thereby obtaining a monoclonal antibody variable light and heavy chain domain encoding nucleic acid,
g) introducing the monoclonal antibody light and heavy chain variable domain encoding nucleic acid in an expression cassette for the expression of an antibody,
h) introducing the nucleic acid in a cell,
i) cultivating the cell and recovering the antibody from the cell or the cell culture supernatant and thereby producing an antibody.

In one embodiment the non-human animal is selected from rat, mouse, hamster, rabbit, non-human primates, sheep, dog, cow, chicken, amphibians, and reptiles.

II. Exemplary Embodiments of the Method According to the Current Invention

The current invention is based at least in part on the finding that EL-4 B5 cells irradiated with a dose of 9.5 Gy or less of gamma irradiation have advantageous properties when used in a B-cell co-cultivation (BCC) method.

The invention is based at least in part on the finding that the irradiation dose applied to EL-4 B5 cells used as feeder cells in the co-cultivation of one or more B-cells can be reduced. Concomitant with the reduction of the irradiation dose also the ratio of EL-4 B5 cells to B-cells has to be reduced and the concentration of the components of the feeder mix have to be adjusted. With this adaptation amongst other things the productivity of the one or more B-cells can be increased and/or the overgrowth of the B-cell by the EL-4 B5 cells can be prevented.

In the art EL-4 B5 cells, like all feeder cells, for use in the co-cultivation of B-cells are first expanded to obtain the required number of cells and thereafter irradiated with a high dose of gamma irradiation in order to inhibit growth of the feeder cells in the thereafter following co-cultivation with B-cells. In the art generally a dose of 50 Gy gamma irradiation is applied to the EL-4 B5 cells. Two days after the irradiation only about one third and seven days after the irradiation on average only about 15% of the cells are vital, i.e. alive.

In more detail, EL-4 B5 cells have been expanded with the method of Example 6. Before γ-irradiation the cell density was adjusted to $10 \times 10^6$ cells/ml. The used dose was 50 Gy. After the irradiation the cells were further cultivated in EL-4 B5 medium. Every day cell number and cell viability (using the ViCell device and trypan blue staining) were determined. The average vitality (relative number of living cells) at the respective days after the irradiation with 50 Gy gamma radiation is presented in the following Table (n=number of data points).

| days after irradiation | n | average viability [%] | SD/2 |
|---|---|---|---|
| 0 | 8 | 86.0 | 4.4 |
| 1 | 6 | 52.8 | 4.9 |
| 2 | 6 | 33.6 | 4.9 |
| 4 | 7 | 22.8 | 4.2 |
| 7 | 8 | 16.0 | 4.6 |

For an average BCC 50.000 irradiated EL-4 B5 cells/well are used. As the maximum cell density in the EL-4 B5 expansion is limited (according to the art the maximum cell density is about $0.5 \times 10^6$ cells/ml) the generation of the required number of non-irradiated EL-4 B5 cells is linked to high cultivation volumes and costs. For example, if three experimental animals are immunized and bled four times about $1 \times 10^9$ EL-4 B5 cells are required for the co-cultivation of all single deposited B-cells.

It has now been found that a reduction of the used gamma radiation dose is possible whereby the number of required non-irradiated EL-4 B5 cells can be significantly reduced as the number of irradiated EL-4 B5 cells in the BCC can be reduced by at least one third or even by up to 80%.

It has further been found that the irradiation of the EL-4 B5 cells can also be completely omitted.

By the reduction of the required non-irradiated EL-4 B5 cell number on the one hand the need for the costly irradiation device and the concomitant safety burdens are no longer required and on the other hand the damage induced in the EL-4 B5 cells by the gamma radiation is reduced. Without being bound by this theory it is assumed that the reduction of the cell damage results in an increased vitality (viability), which, in turn, allows for the reduction of the number of EL-4 B5 feeder cells used in the co-cultivation with B-cells. This results in improved cultivation conditions.

Thus, one aspect as reported herein is a method for co-cultivating one or more B-cells comprising the step of
co-cultivating the one or more B-cells with EL-4 B5 cells,
whereby the EL-4 B5 cells have been irradiated with gamma radiation prior to the co-cultivation with a dose of 9.5 Gy or less.

In one embodiment the irradiation is with a dose in the range of about 3 Gy to about 7 Gy. In one embodiment the irradiation is with a dose in the range of about 3 Gy to about 6 Gy. In one embodiment the irradiation is with a dose in the range of about 3 Gy to about 5 Gy. In one preferred embodiment the irradiation is with a dose of about 4 Gy.

In one embodiment the co-cultivating of the one or more B-cells is with 30,000 EL-4 B5 cells or less. In one embodiment the co-cultivating is with 5,000 to 30,000 EL-4 B5 cells. In one embodiment the co-cultivating is with 10,000 to 30,000 EL-4 B5 cells.

In one preferred embodiment the co-cultivating of the one or more B-cells is with about 10,000 to about 30,000 EL-4 B5 cells, which have been irradiated with gamma radiation of a dose in the range of about 3 Gy to about 6 Gy.

In one embodiment the co-cultivating is in the presence of TSN. In one embodiment the co-cultivating is in the presence of up to 5 vol-% TSN. In one embodiment the co-cultivating is in the presence of about 1.25 vol-% to about 3.75 vol-% TSN. In one preferred embodiment the co-cultivating is in the presence of about 2.5 vol-% TSN.

In one embodiment the co-cultivating is in the presence of a feeder-mix (cytokine-mix, CM).

In one embodiment the feeder mix comprises
(up to) about 2 ng/ml (murine) IL-1beta,
(up to) about 2 ng/ml (murine) TNFalpha,
(up to) about 50 ng/ml (murine) IL-2,
(up to) about 10 ng/ml (murine) IL-10, and
(up to) about 10 ng/ml (murine) IL-6,
or a fraction thereof.

In one embodiment the feeder mix comprises
(up to) about 2 ng/ml with 5.5-14*$10^8$ IU/mg (murine) IL-1beta,
(up to) about 2 ng/ml with 2.3-2.9*$10^8$ U/mg (murine) TNFalpha,
(up to) about 50 ng/ml with 6-7 (preferably 6.3)*$10^6$ IU/mg (murine) IL-2,
(up to) about 10 ng/ml with 6-7.5*$10^5$ IU/mg (murine) IL-10, and
(up to) about 10 ng/ml with 9.2-16.1*$10^8$ U/mg (murine) IL-6,
or a fraction thereof.

In one embodiment the fraction of the feeder mix is selected from the group of fractions consisting of 0.75, 0.5, 0.32, 0.25, 0.1, 0.066, 0.032, 0.015, 0.01, 0.0075, 0.0038. In one embodiment the fraction of the feeder mix is in the range of from 1.0 to 0.015. In one preferred embodiment the fraction of the feeder mix is in the range of from 0.1 to 0.015.

In one embodiment the co-cultivation is in the presence of about 0.3 ng/ml-3 ng/ml phorbol myristate acetate.

In one embodiment the feeder mix further comprises about 0.01 ng/ml-1.5 ng/ml phorbol myristate acetate. In one embodiment the feeder mix further comprises about 0.125 ng/ml-1 ng/ml phorbol myristate acetate. In one preferred embodiment the feeder mix further comprises about 0.25 ng/ml-0.5 ng/ml phorbol myristate acetate.

In one embodiment the fraction of the feeder mix is in the range of from 0.1 to 0.015 and the feeder mix further comprises about 0.01 ng/ml-1.0 ng/ml phorbol myristate acetate. In one preferred embodiment the fraction of the feeder mix is about 0.03 and the feeder mix further comprises about 0.25 ng/ml-0.5 ng/ml phorbol myristate acetate.

In one preferred embodiment the co-cultivating of the one or more B-cells is with about 10,000 to about 30,000 EL-4 B5 cells, which have been irradiated with gamma radiation of a dose in the range of about 3 Gy to about 6 Gy (preferably about 4 Gy), wherein the feeder mix comprises about 0.06 ng/ml (murine) IL-1 beta, about 0.06 ng/ml (murine) TNFalpha, about 1.5 ng/ml (murine) IL-2, about 0.3 ng/ml (murine) IL-10, about 0.3 ng/ml (murine) IL-6, and about 0.25 ng/ml-0.5 ng/ml PMA.

In one preferred embodiment the co-cultivating of the one or more B-cells is with about 2,500 to about 7,500 EL-4 B5 cells (preferably about 5,000), which have been irradiated with gamma radiation of a dose in the range of 0 Gy to less than 3 Gy, wherein the feeder mix fraction is 0.03 to 0.1 (the feeder mix comprises about 0.06 ng/ml to about 0.2 ng/ml (murine) IL-1beta, about 0.06 ng/ml to about 0.2 ng/ml (murine) TNFalpha, about 1.5 ng/ml to about 5 ng/ml (murine) IL-2, about 0.3 ng/ml to about 1 ng/ml (murine) IL-10, about 0.3 ng/ml to about 1 ng/ml (murine) IL-6, and about 0.43 ng/ml-0.73 ng/ml PMA (preferably 0.73 ng/ml).

For each irradiation dose a respective feeder cell number, feeder mix fraction as well as PMA concentration can be identified.

In more detail, EL-4 B5 cells have been expanded with the method according to Example 6. Thereafter, aliquots thereof have been subjected to a single gamma irradiation with different irradiation doses ranging from 0.5 to 50 Gy. Additionally, non-irradiated EL-4 B5 cells have been included. All samples were cultivated independently in EL-4 B5 cultivation medium for additional 7 days. The vitality (viability) as well as the absolute cell number have been determined on a daily basis (using the ViCell device and trypan blue staining). The results are shown in the following Tables (n.d.=not determined; all but 3 Gy, 5 Gy and 50 Gy have been determined in the same experiment).

viability/vitality [%]:

| | irradiation dose | | | | | | | | | |
|---|---|---|---|---|---|---|---|---|---|---|
| day after irradiation | 0 Gy (no irradiation) | 0.5 Gy | 2 Gy | 3 Gy | 4 Gy | 5 Gy | 6 Gy | 8 Gy | 10 Gy | 50 Gy (reference) |
| 0 (reference) | 87.5 | 86.7 | 83.9 | 79.6 | 86.3 | 85.7 | 89 | 88.6 | 88.6 | 87.2 |
| 1 | 90 | 92.5 | 84.6 | 76.7 | 70.7 | 67.9 | 67.2 | 59 | 58.2 | 60.7 |
| 2 | 93 | 89.9 | 79.8 | 69.7 | 58 | 53.1 | 44.3 | 35.3 | 32.4 | 31.7 |
| 3 | 78.8 | 81.1 | 77 | 70.2 | 54.9 | 48 | 33.2 | 26.8 | 23.7 | 25.3 |

-continued

| day after irradiation | 0 Gy (no irradiation) | 0.5 Gy | 2 Gy | 3 Gy | 4 Gy | 5 Gy | 6 Gy | 8 Gy | 10 Gy | 50 Gy (reference) |
|---|---|---|---|---|---|---|---|---|---|---|
| | | | | | irradiation dose | | | | | |
| 4 | 41.5 | 47.9 | 71.4 | n.d. | 53.2 | n.d. | 25.4 | 20.9 | 17.8 | n.d. |
| 6 | n.d. | n.d. | n.d. | 58.1 | n.d. | 63 | n.d. | n.d. | n.d. | 19.3 |
| 7 | 16.6 | 16.5 | 18.3 | 38.3 | 48.7 | 71.6 | 47.2 | 17.6 | 15.1 | 14.2 | total cell number [n*10$^5$]: 0 Gy, 0.5 Gy, 2 Gy, 4 Gy, 6 Gy, 8 Gy, 10 Gy (Experiment 1); 3 Gy, 5 Gy, 50 Gy (Experiment 2):

| day after irradiation | 0 Gy (no irradiation) | 0.5 Gy | 2 Gy | 3 Gy | 4 Gy | 5 Gy | 6 Gy | 8 Gy | 10 Gy | 50 Gy (reference) |
|---|---|---|---|---|---|---|---|---|---|---|
| | | | | | irradiation dose | | | | | |
| 0 (reference) | 4.5 | 3.9 | 3.8 | 2.5 | 3.8 | 2.8 | 3.7 | 3.4 | 3.7 | 2.8 |
| 1 | 9.7 | 8.7 | 7.3 | 4.6 | 5.9 | 4.8 | 5.3 | 4.9 | 4.8 | 3 |
| 2 | 23.4 | 20.9 | 13.2 | 6.9 | 7.9 | 4.9 | 5.5 | 4.5 | 4.3 | 2.9 |
| 3 | 41.5 | 37.6 | 22.2 | 9.5 | 9.5 | 5 | 5.6 | 5 | 4.6 | 2.5 |
| 4 | 41.6 | 40.5 | 31.9 | n.d. | 11.8 | n.d. | 5.8 | 4.7 | 4.5 | n.d. |
| 6 | n.d. | n.d. | n.d. | 29.3 | n.d. | 11.4 | n.d. | n.d. | n.d. | 2.7 |
| 7 | 40.8 | 41.3 | 33.9 | 28.8 | 28.5 | 18.1 | 9.2 | 4.6 | 4.4 | 2.6 | relative proliferation calculated as ratio of the total cell number at day x and the total cell number at day 0 (dx/d0):

| day after irradiation | 0 Gy (no irradiation) | 0.5 Gy | 2 Gy | 3 Gy | 4 Gy | 5 Gy | 6 Gy | 8 Gy | 10 Gy | 50 Gy (reference) |
|---|---|---|---|---|---|---|---|---|---|---|
| | | | | | irradiation dose | | | | | |
| 0 (reference) | 1 | 1 | 1 | 1 | 1 | 1 | 1 | 1 | 1 | 1 |
| 1 | 2.16 | 2.23 | 1.92 | 1.84 | 1.55 | 1.71 | 1.43 | 1.44 | 1.30 | 1.07 |
| 2 | 5.20 | 5.36 | 3.47 | 2.76 | 2.08 | 1.75 | 1.49 | 1.32 | 1.16 | 1.04 |
| 3 | 9.22 | 9.64 | 5.84 | 3.80 | 2.50 | 1.79 | 1.51 | 1.47 | 1.24 | 0.89 |
| 4 | 9.24 | 10.38 | 8.39 | n.d. | 3.11 | n.d. | 1.57 | 1.38 | 1.22 | n.d. |
| 6 | n.d. | n.d. | n.d. | 11.72 | n.d. | 4.07 | n.d. | n.d. | n.d. | 0.96 |
| 7 | 9.07 | 10.59 | 8.92 | 11.52 | 7.50 | 6.46 | 2.49 | 1.35 | 1.19 | 0.93 |

Figure 1:
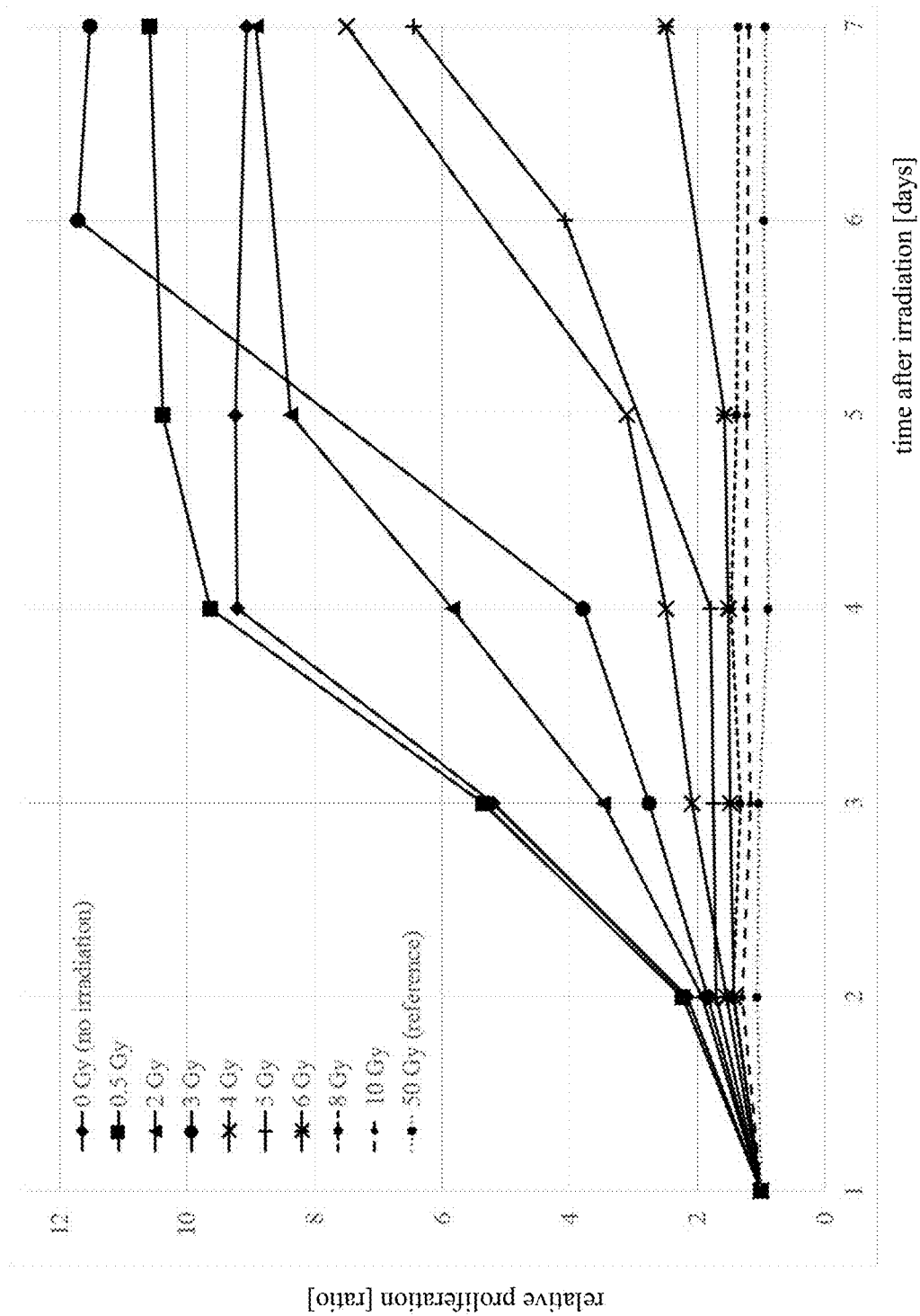
FIG. 1 Relative proliferation of EL-4 B5 cells (calculated as a ratio of the total cell number at day x and the total cell number at day 0 (dx/d0)) determined over a time span of 7 days after irradiation with doses from 0 Gy-50 Gy.

The course of the relative proliferation is shown in FIG. 1.

Figure 2:
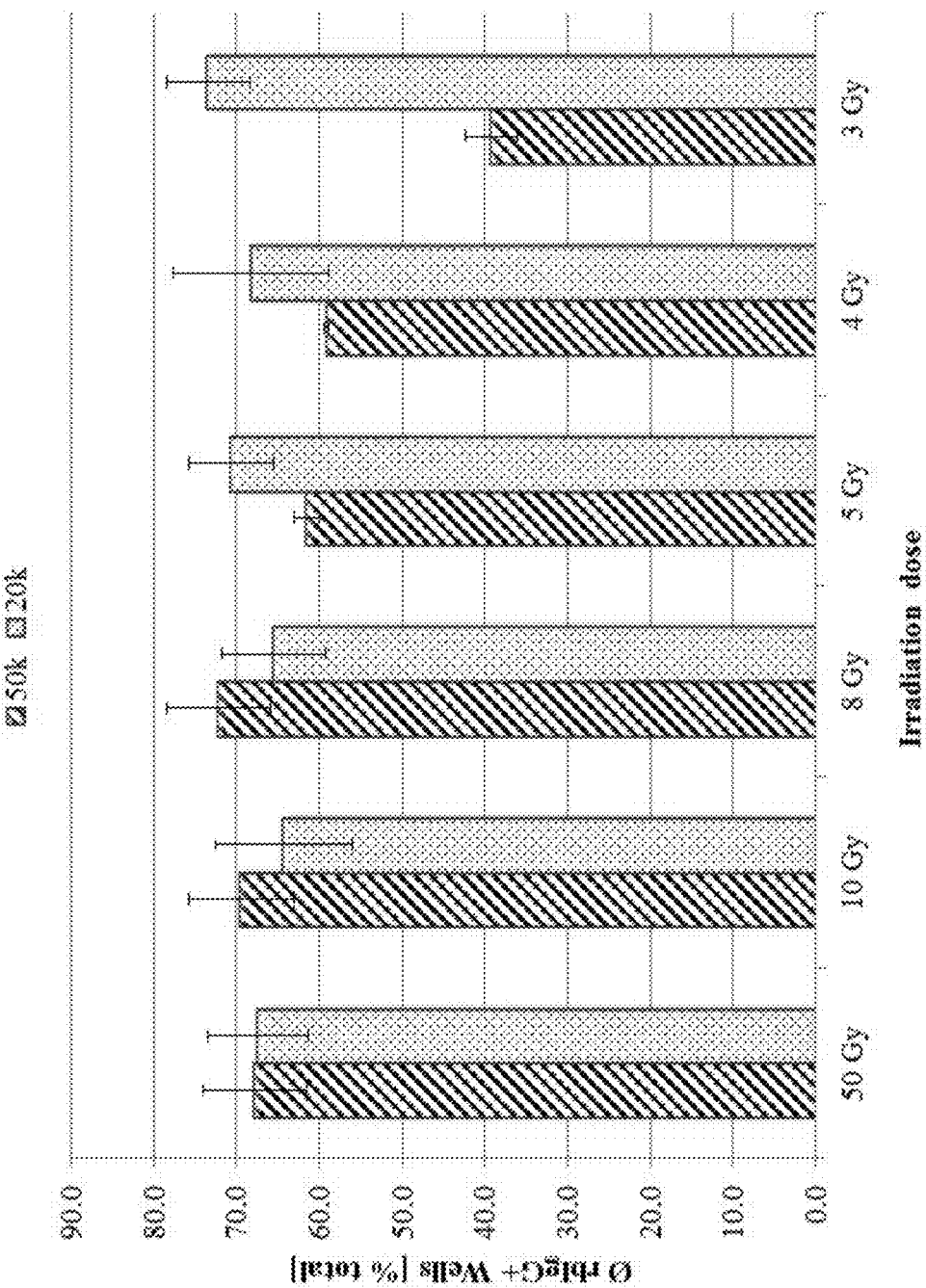
FIG. 2 Frequency of rbIgG+ wells (rabbit IgG positive wells) in % of total wells after co-culture of single deposited B-cells with 20,000 (20 k) or 50,000 (50 k) EL-4 B5 cells irradiated with 3 Gy, 4 Gy, 5 Gy, 8 Gy, 10 Gy, or 50 Gy, respectively. The average with SD of three 96-well plates is shown.
Figure 3:
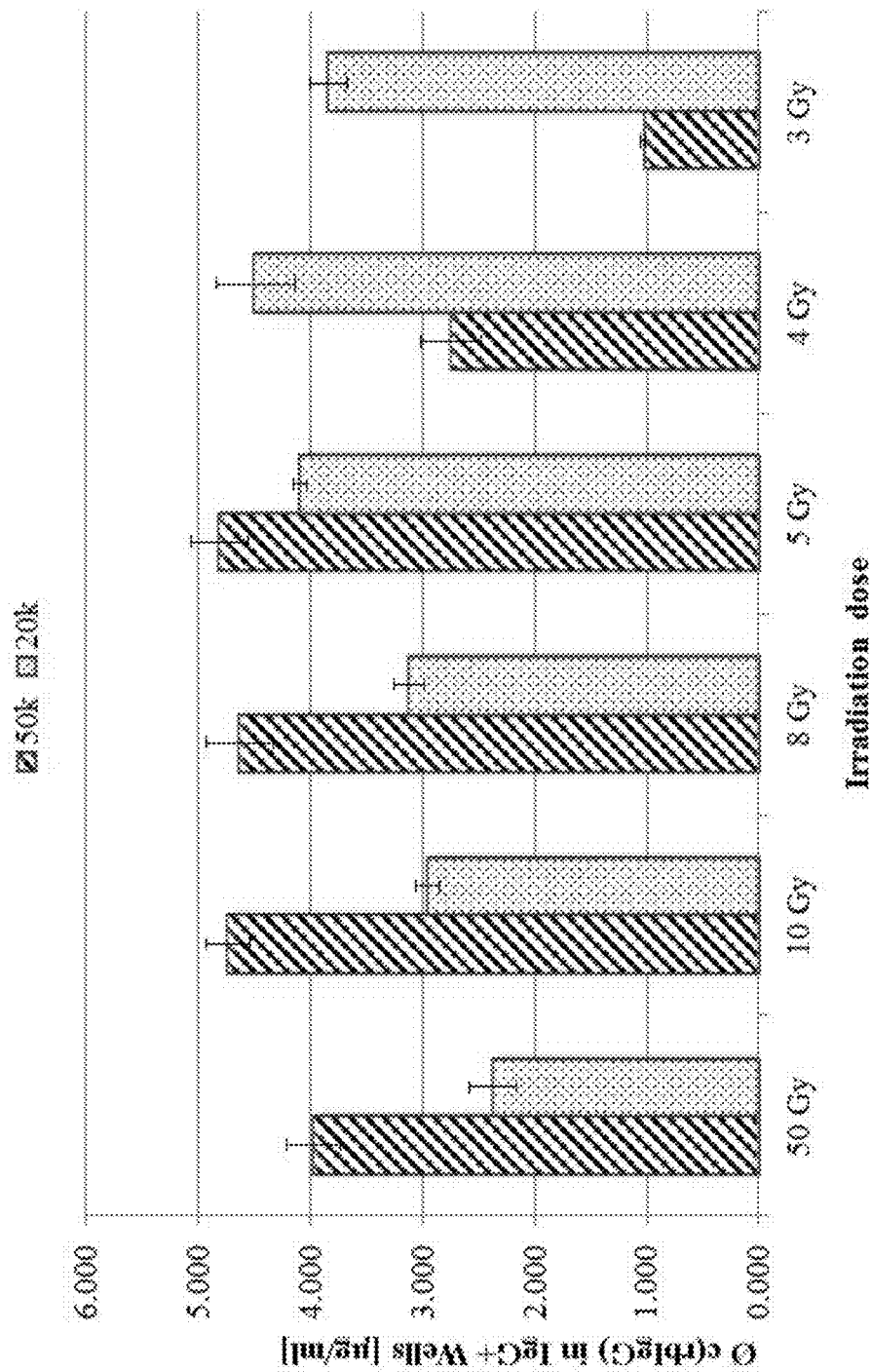
FIG. 3 Average IgG-concentration of IgG-secreting B-cell clones (single deposited B-cell progeny), i.e. productivity, in µg/ml after a co-culture of single deposited B-cells with 20 k or 50 k EL-4 B5 cells irradiated with 3 Gy, 4 Gy, 5 Gy, 8 Gy, 10 Gy, or 50 Gy, respectively. The average with SD of three 96-well plates is shown.

EL-4 B5 cells that have been irradiated with a dose of 3 Gy, 4 Gy, 5 Gy, 8, Gy, and 10 Gy have been employed in the B-cell co-cultivation (BCC) of single deposited B-cells obtained (macrophage depleted) from a non-immunized wild-type rabbit according to Example 8. The employed number of EL-4 B5 cell per single deposited B-cell was 50,000 and 20,000, respectively. The average results (taken from three 96-well plates) are shown in the following Tables and in FIGS. 2 and 3. The IgG in the supernatant has been determined using the assay of Example 9.

average values:

| | EL-4 B5 cells | | | |
|---|---|---|---|---|
| | 50,000 | 20,000 | 50,000 | 20,000 |
| | frequency | | productivity | |
| irradiation dose | Ø rbIgG-positive wells [% total] | | Ø c(rbIgG) IgG+ Wells [µg/ml] | |
| 50 Gy | 67.9 | 67.5 | 3.968 | 2.372 |
| 10 Gy | 69.4 | 64.3 | 4.737 | 2.957 |
| 8 Gy | 72.2 | 65.5 | 4.623 | 3.118 |

-continued

| | EL-4 B5 cells | | | |
|---|---|---|---|---|
| | 50,000 | 20,000 | 50,000 | 20,000 |
| | frequency | | productivity | |
| irradiation dose | Ø rbIgG-positive wells [% total] | | Ø c(rbIgG) IgG+ Wells [µg/ml] | |
| 5 Gy | 61.5 | 70.6 | 4.810 | 4.083 |
| 4 Gy | 59.1 | 68.3 | 2.739 | 4.487 |
| 3 Gy | 39.3 | 73.4 | 1.030 | 3.831 | standard deviation (SD/2):

| | EL-4 B5 cells | | | |
|---|---|---|---|---|
| | 50,000 | 20,000 | 50,000 | 20,000 |
| | frequency | | productivity | |
| irradiation dose | Ø rbIgG-positive wells [% total] | | Ø c(rbIgG) IgG+ Wells [µg/ml] | |
| 50 Gy | 6.3 | 6.1 | 0.235 | 0.212 |
| 10 Gy | 6.4 | 8.2 | 0.193 | 0.103 |

-continued

| | EL-4 B5 cells | | | |
|---|---|---|---|---|
| | 50,000 | 20,000 | 50,000 | 20,000 |
| | frequency | | productivity | |
| irradiation dose | Ø rbIgG-positive wells [% total] | | Ø c(rbIgG) IgG+ Wells [µg/ml] | |
| 8 Gy | 6.3 | 6.3 | 0.301 | 0.140 |
| 5 Gy | 1.5 | 5.1 | 0.251 | 0.059 |
| 4 Gy | 0.3 | 9.5 | 0.270 | 0.356 |
| 3 Gy | 3.1 | 5.0 | 0.026 | 0.163 |

From the data can be seen that with lower irradiation dose the number of EL-4 B5 cells has to be reduced to achieve an improved growth rate and productivity compared to the standard value of 50,000 EL-4 B5 cells per single deposited B-cell.

Figure 4:
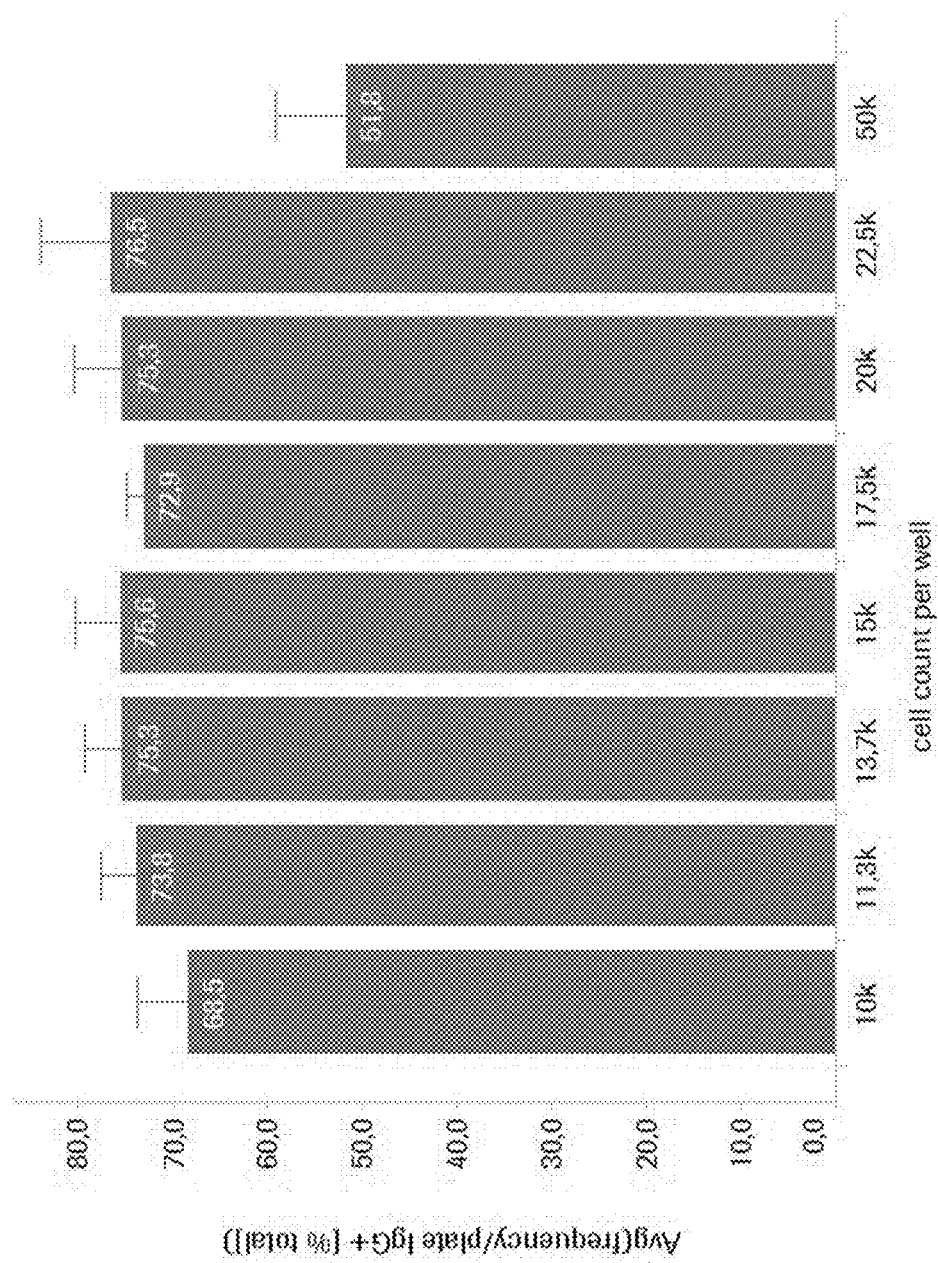
FIG. 4 Frequency of rbIgG+ wells in % of total wells after co-culture of single deposited B-cells with different EL-4 B5 cell counts (4 Gy irradiated) of 10 k-50 k/well. The average with SD of four 96-well plates is shown.
Figure 5:
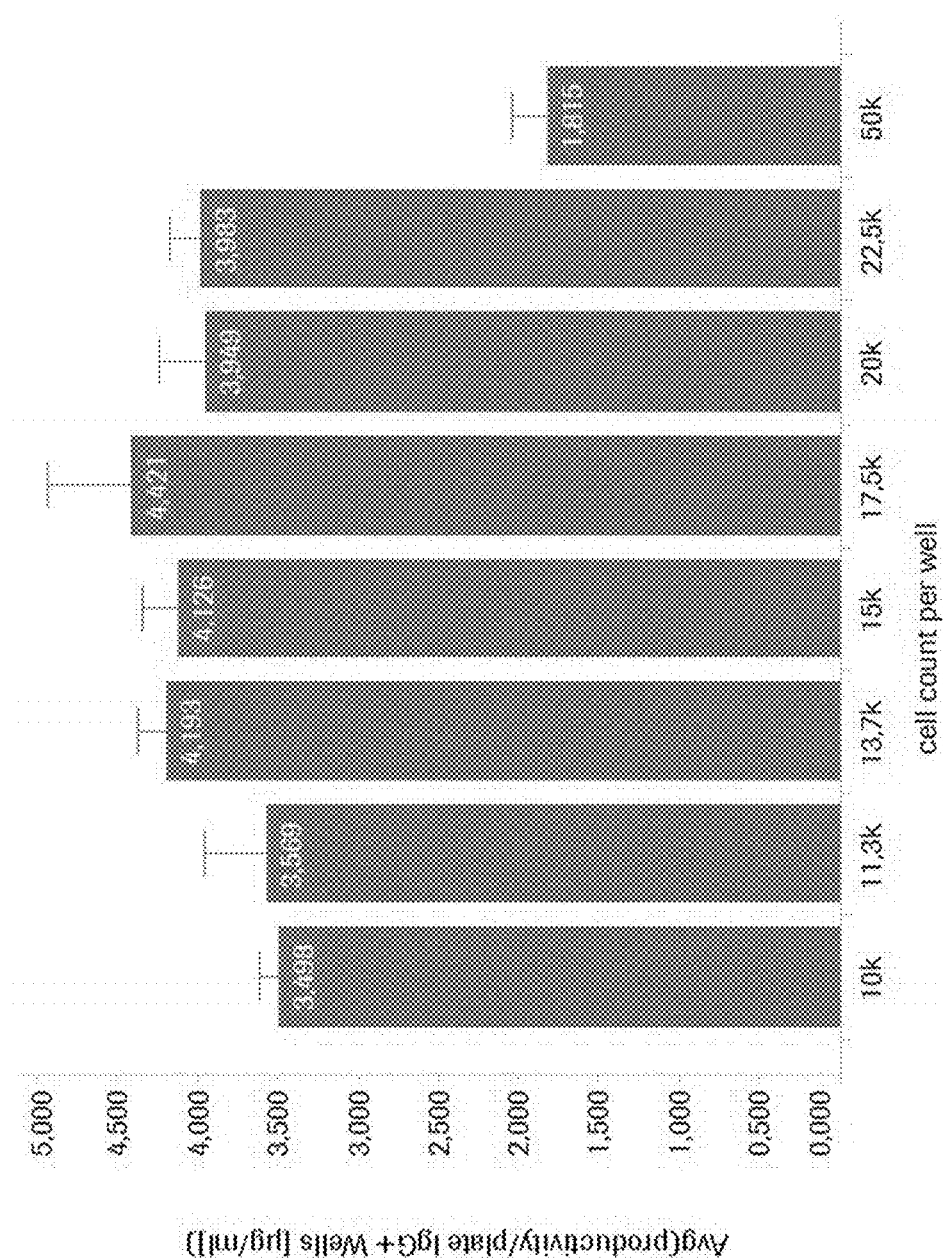
FIG. 5 Average IgG-concentration of IgG-secreting B-cell clones (single deposited B-cell progeny), i.e. productivity, in µg/ml after a co-culture of single deposited B-cells with different EL-4 B5 cell counts (4 Gy irradiated) of 10 k-50 k/well. The average with SD of four 96-well plates is shown.

EL-4 B5 cells that have been irradiated with a dose of 4 Gy have been employed in the B-cell co-cultivation (BCC) of single deposited B-cells (macrophage depleted) obtained from a non-immunized wild-type rabbit according to Example 8. The employed number of EL-4 B5 cell per single deposited B-cell was between 10,000 and 50,000, respectively. The average results (taken from four 96-well plates; average of value of plates which is average value of wells on the plate) are shown in the following Tables and in FIG. 4 and FIG. 5. The IgG in the supernatant has been determined using the assay of Example 9.

average values:

| | 4 Gy frequency EL-4 B5 cells/well | |
|---|---|---|
| irradiation dose | Ø rbIgG-positive wells [% total] | SD |
| 10,000 | 68.5 | 3.498 |
| 11,300 | 73.8 | 3.569 |
| 13,700 | 75.3 | 4.193 |
| 15,000 | 75.6 | 4.126 |
| 17,500 | 72.9 | 4.421 |
| 20,000 | 75.3 | 3.949 |
| 22,500 | 76.5 | 3.983 |
| 50,000 | 51.8 | 1.815 |

| | 4 Gy | |
|---|---|---|
| | productivity EL-4 B5 cells/well | |
| irradiation dose | Ø c(rbIgG) IgG+ Wells [µg/ml] | SD |
| 10,000 | 4.65 | 0.097 |
| 11,300 | 3.26 | 0.340 |
| 13,700 | 3.41 | 0.157 |
| 15,000 | 3.99 | 0.196 |
| 17,500 | 1.76 | 0.442 |
| 20,000 | 4.40 | 0.258 |
| 22,500 | 6.38 | 0.169 |
| 50,000 | 6.33 | 0.190 |

It can be seen that in the range up to 22,500 EL-4 B5 cells per well and B-cell comparable values can be obtained, wherein the range from 11,300 to 22,500 is preferred with respect to growth rate. With respect to IgG production the range from 13,700 to 22,500 is preferred.

Figure 6:
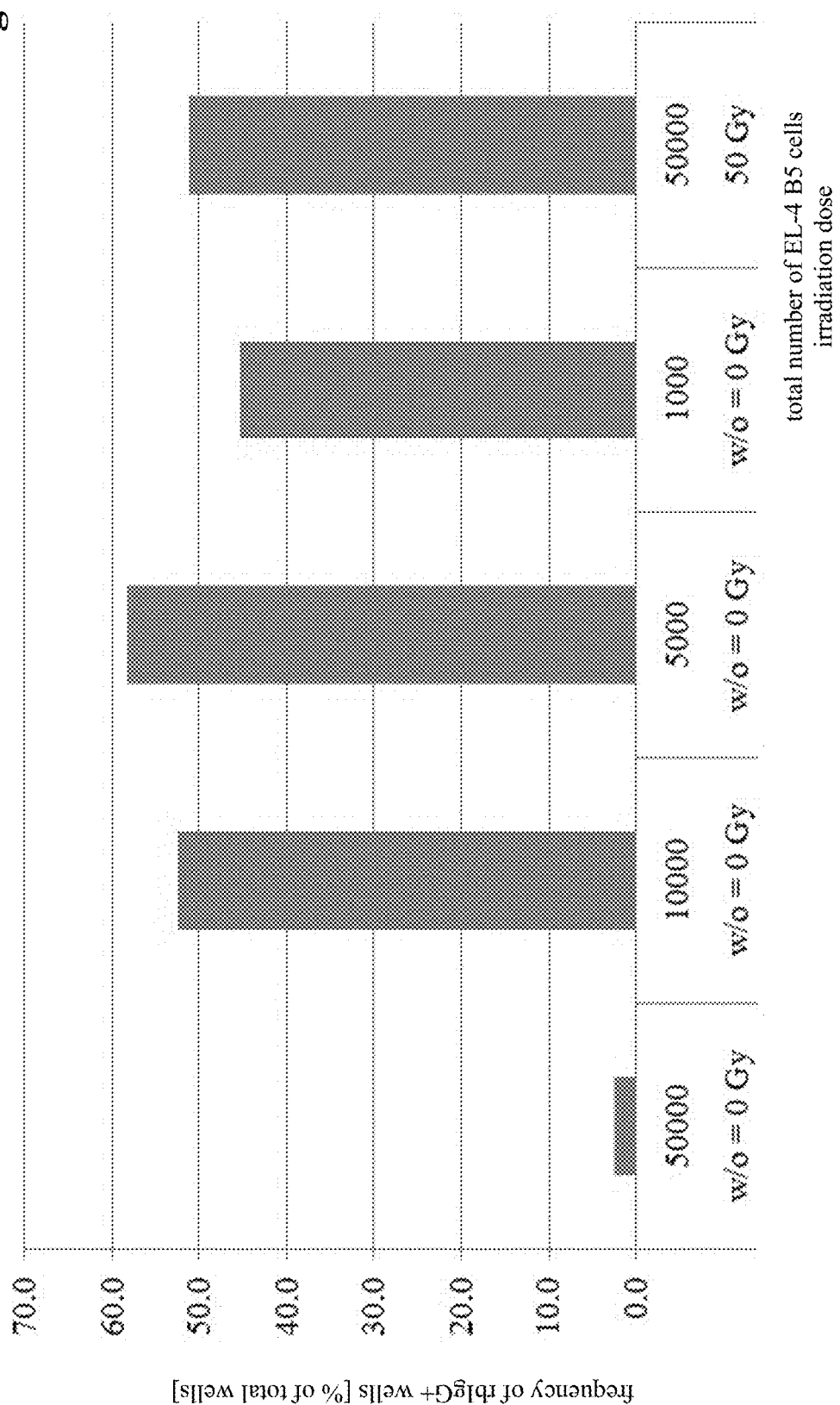
FIG. 6 Frequency of rbIgG+ wells in % of total wells after co-culture of single deposited B-cells with different cell counts of 1 k-50 k/well of non-irradiated EL-4 B5 cells. A cultivation with 50 Gy irradiated EL-4 B5 cells with a cell count of 50 k/well served as positive control.

This experiment has been done also with non-irradiated EL-4 B5 cells. The results are shown in the following Tables and FIG. 6. For reference the example with 50,000 EL-4 B5 cells irradiated with 50 Gy are shown.

average values:

| | 0 Gy = no irradiation | |
|---|---|---|
| | frequency | productivity |
| | EL-4 B5 cells/well | |
| irradiation dose | Ø rbIgG-positive wells [% total] | Ø c(rbIG) IgG+ Wells [µg/ml] |
| 50,000 | 2.4 | 0.1 |
| 10,000 | 52.4 | 0.4 |
| 5,000 | 58.3 | 0.8 |
| 1,000 | 45.2 | 0.6 |

| | 50 Gy = reference | |
|---|---|---|
| | frequency | productivity |
| | EL-4 B5 cells/well | |
| irradiation dose | Ø rbIgG-positive wells [% total] | Ø c(rbIG) IgG+ Wells [µg/ml] |
| 50,000 | 51.2 | 1.5 |

It can be seen that for non-irradiated EL-4 B5 cells the number of cells per well and per single deposited B-cell has to be reduced to about 10,000 cells or less.

In the next experiment B-cells obtained from a wild-type rabbit according to Examples 2 and 3 that had been immunized with human VEGF according to Example 1 were used in the BCC. The B-cells had been pre-treated according to Example 4 with biotinylated human VEGF conjugated to biotin as capture reagent. EL-4 B5 cells that have been irradiated with a dose of 4 Gy have been employed in the B-cell co-cultivation (BCC) of the single deposited B-cell according to Example 8. The employed number of EL-4 B5 cell per single deposited B-cell was between 12,500 and 30,000, respectively. The average results (taken from three 96-well plates) are shown in the following Tables. The IgG in the supernatant has been determined using the assay of Example 9. For reference the example with 50,000 EL-4 B5 cells irradiated with 50 Gy are shown.

average values:

| | 4 Gy frequency EL-4 B5 cells/well | |
|---|---|---|
| irradiation dose | Ø rbIgG-positive wells [% total] | SD |
| 12,500 | 11.9 | 2.9 |
| 17,500 | 11.9 | 2.6 |
| 22,500 | 15.1 | 2.9 |
| 30,000 | 15.1 | 2.5 |

| | 50 Gy frequency EL-4 B5 cells/well | |
|---|---|---|
| irradiation dose | Ø rbIgG-positive wells [% total] | SD |
| 50,000 | 11.1 | 2.5 |

| | 4 Gy productivity EL-4 B5 cells/well | |
|---|---|---|
| irradiation dose | Ø c(rbIgG) IgG+ Wells [µg/ml] | SD |
| 12,500 | 0.9 | 0.39 |
| 17,500 | 1.6 | 0.20 |

-continued

| | 50 Gy productivity EL-4 B5 cells/well | |
|---|---|---|
| 22,500 | 1.3 | 0.69 |
| 30,000 | 1.2 | 0.22 |

| | 50 Gy productivity EL-4 B5 cells/well | |
|---|---|---|
| irradiation dose | Ø c(rbIgG) IgG+ Wells [µg/ml] | SD |
| 50,000 | 1.6 | 1.11 |

Figure 7:
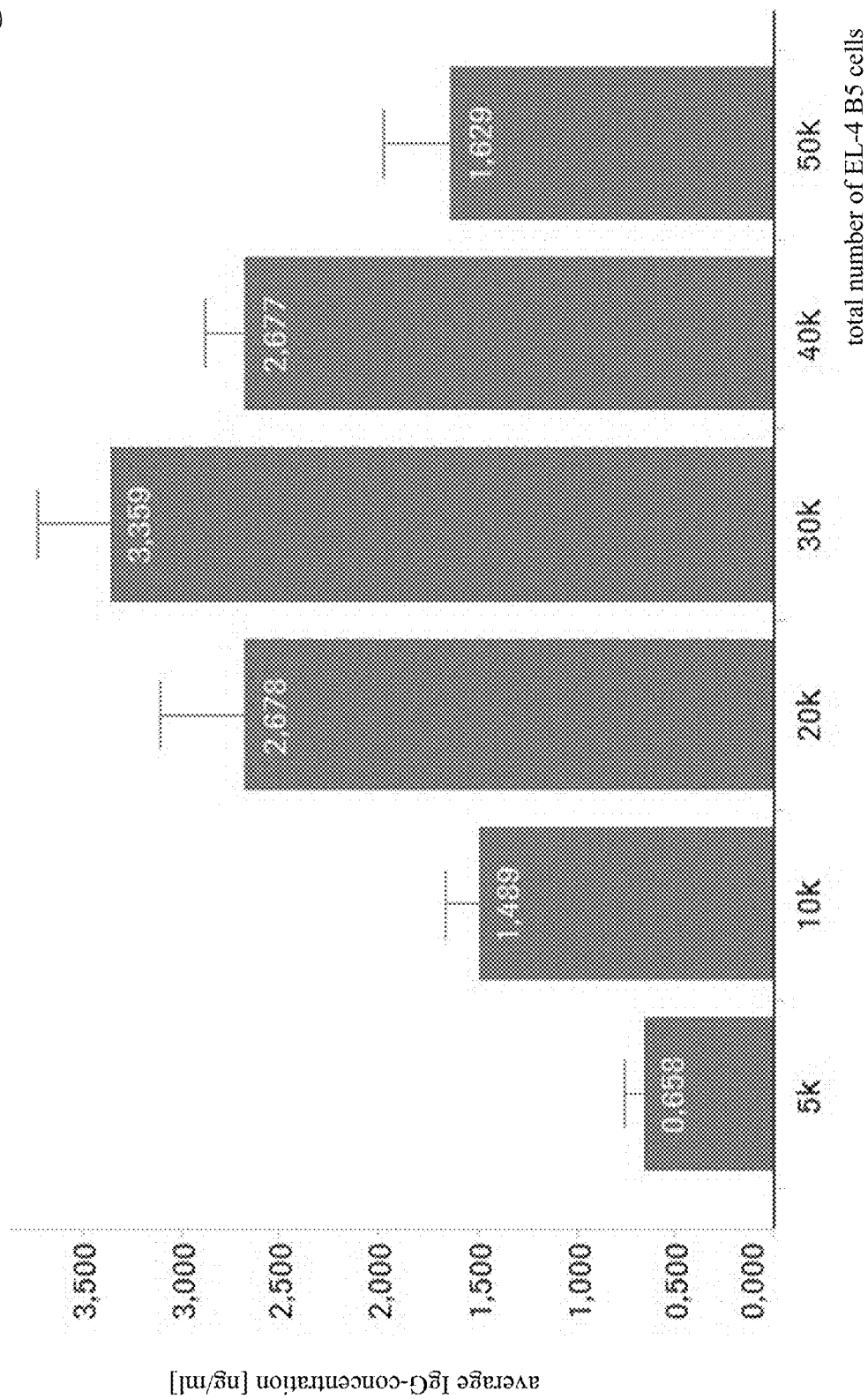
FIG. 7 Average IgG-concentration of IgG-secreting B-cell clones (single deposited B-cell progeny), i.e. productivity, in µg/ml after a co-culture of single deposited B-cells with different EL-4 B5 counts (4 Gy irradiated) of 10 k-50 k/well. The average with SD of four 96-well plates is shown.

The experiment has been repeated with B-cells obtained from a wild-type rabbit according to Examples 2 and 3 that had been immunized with human serum albumin (HSA) according to Example 1 were used in the BCC. The B-cells had been pre-treated according to Example 4. EL-4 B5 cells that have been irradiated with a dose of 4 Gy have been employed in the B-cell co-cultivation (BCC) of the single deposited B- according to Example 8). The employed number of EL-4 B5 cell per single deposited B-cell was between 5,000 and 50,000, respectively. The average results (taken wells from four 96-well plates) are shown in the following Tables and FIG. 7 (productivity data). The IgG in the supernatant has been determined using the assay of Example 9.

average values:

| | 4 Gy frequency EL-4 B5 cells/well | |
|---|---|---|
| irradiation dose | Ø rbIgG-positive wells [% total] | SD |
| 5,000 | 69.1 | 5.89 |
| 10,000 | 62.8 | 8.50 |
| 20,000 | 71.7 | 7.89 |
| 30,000 | 70.3 | 12.59 |
| 40,000 | 62.2 | 5.26 |
| 50,000 | 50.9 | 1.77 |

| | 4 Gy productivity EL-4 B5 cells/well | |
|---|---|---|
| irradiation dose | Ø c(rbIgG) IgG+ Wells [µg/ml] | SD |
| 5,000 | 0.658 | 0.082 |
| 10,000 | 1.489 | 0.145 |
| 20,000 | 2.678 | 0.367 |
| 30,000 | 3.359 | 0.316 |
| 40,000 | 2.677 | 0.174 |
| 50,000 | 1.629 | 0.298 |

In the next experiments the influence of the feeder mix has been examined.

Figure 8:
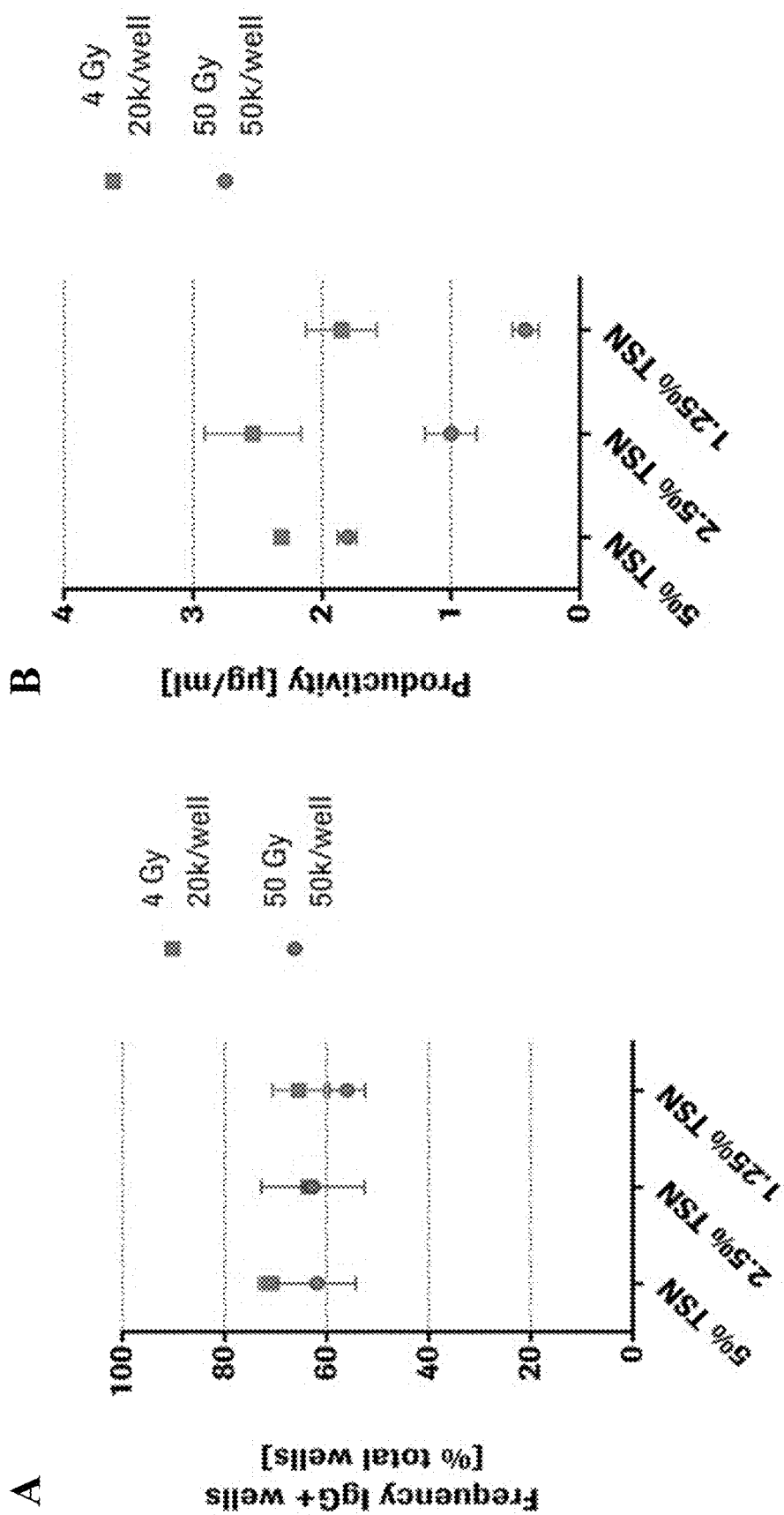
FIG. 8 Interrelation of the irradiation dose of the feeder cells and the TSN (natural species-specific feeder mix) concentration on the yield of the B-cell clones.

At first the natural feeder mix TSN had been used. In this experiment EL-4 B5 cells irradiated with a dose of 4 Gy and 50 Gy, respectively, had been co-cultivated with single deposited B-cells obtained from a non-immunized wild-type rabbit according to Example 8. The results are shown in the Tables below as well as in FIG. 8.

| | c (TSN) | frequency/plate rbIgG+ [% total] | average prod./plate, IgG+ wells [µg/ml] |
|---|---|---|---|
| EL-4 B5 20,000 4 Gy | 5% TSN | 69.0 | 2.379 |
| | | 71.4 | 2.272 |
| | | 73.8 | 2.301 |
| | 2.5% TSN | 65.5 | 2.387 |
| | | 63.1 | 2.179 |
| | | 61.9 | 3.054 |
| | 1.25% TSN | 63.1 | 1.975 |
| | | 60.7 | 1.476 |
| | | 72.6 | 2.113 |
| EL-4 B5 50,000 50 Gy | 5% TSN | 57.1 | 1.717 |
| | | 72.6 | 1.896 |
| | | 56.0 | 1.814 |
| | 2.5% TSN | 48.8 | 0.837 |
| | | 66.7 | 1.256 |
| | | 72.6 | 0.908 |
| | 1.25% TSN | 54.8 | 0.273 |
| | | 52.4 | 0.455 |
| | | 60.7 | 0.538 |

It can be seen that for EL-4 B5 cells irradiated with the reduced dose of 4 Gy the required amount of TSN can be reduced from 5% to 1.25% to 2.5% and still the same frequency of IgG positive wells as well as the same productivity per well can be obtained as with the EL-4 B5 cells irradiated with a dose of 50 Gy and 5% TSN. Thus, the required amount of expensive TSN can be at least reduced by 50%.

The same experiment has been done with non-irradiated EL-4 B5 cells. The results are shown in the following Table (total wells=84).

| irradiation | Feeder cells | TSN [%] | rbIgG+ [n] | frequency IgG+ [% total wells] | average IgG conc. of IgG+ wells [µg/ml] |
|---|---|---|---|---|---|
| w/o = 0 Gy | 10,000 | 5 | 64 | 76.2 | 1.781 |
| w/o = 0 Gy | 5,000 | 5 | 69 | 82.1 | 2.262 |
| w/o = 0 Gy | 5,000 | 2.5 | 45 | 53.6 | 0.364 |
| w/o = 0 Gy | 5,000 | 1.25 | 24 | 28.6 | 0.126 |
| 50 Gy | 50,000 | 5 | 65 | 77.4 | 3.459 |

Also the effect of a defined (synthetic) cytokine mix (CM) as feeder mix has been tested. In this experiment EL-4 B5 cells irradiated with a dose of 4 Gy and 50 Gy, respectively, had been co-cultivated with single deposited B-cells (macrophage depleted) obtained from a non-immunized wild-type rabbit according to Example 8. In total wells from three 96 well plates have been analyzed. The results are shown in the Tables below as well as in FIG. 9 and FIG. 10.

| irradiation dose/cell count/well | c (CM) | frequency/plate rbIgG+ [% total] | SD | average prod./plate, IgG+ wells [µg/ml] | SD |
|---|---|---|---|---|---|
| 50 Gy 50,000/well | 1x CM | 53.6 | 7.6 | 2.200 | 0.089 |
| | 0.75x CM | 66.3 | 3.1 | 1.758 | 0.444 |
| | 0.5x CM | 57.5 | 6.8 | 1.540 | 0.176 |
| | 0.25x CM | 55.6 | 1.1 | 1.045 | 0.084 |
| | 0.1x CM | 57.1 | 2.9 | 0.563 | 0.040 |
| 4 Gy 20,000/well | 1x CM | 58.7 | 2.8 | 1.377 | 0.151 |
| | 0.75x CM | 63.9 | 4.8 | 2.278 | 0.359 |
| | 0.5x CM | 66.3 | 1.1 | 2.949 | 0.184 |
| | 0.25x CM | 67.5 | 2.8 | 2.585 | 0.269 |
| | 0.1x CM | 65.9 | 3.0 | 1.974 | 0.321 |

| irradiation dose/cell count/well | c (CM) | frequency/ plate rbIgG+ [% total] | SD | average prod./plate, IgG+ wells [µg/ml] | SD |
|---|---|---|---|---|---|
| 50 Gy 50,000/well | 0.1x CM | 35.7 | 2.6 | 0.930 | 0.216 |
| | 0.066x CM | 36.5 | 7.9 | 0.679 | 0.063 |
| | 0.032x CM | 36.9 | 7.6 | 0.501 | 0.085 |
| | 0.01x CM | 32.9 | 4.8 | 0.216 | 0.039 |
| 4 Gy 20,000/well | 0.1x CM | 44.4 | 2.0 | 2.860 | 0.504 |
| | 0.066x CM | 44.8 | 3.4 | 2.760 | 0.124 |
| | 0.032x CM | 40.1 | 12.5 | 3.215 | 0.416 |
| | 0.01x CM | 40.5 | 6.1 | 2.498 | 0.346 |

From the data it can be seen that 4 Gy irradiated EL-4 B5 feeder cells provide higher growth rates as 50 Gy irradiated EL-4 B5 cells. With respect to single well productivity it can be seen that 50 Gy irradiated EL-4 B5 cells require a higher concentration of the cytokine mix (highest productivity with 1×CM). EL-4 B5 cells irradiated with a dose of 4 Gy show the highest productivity at about 0.03×CM, i.e. at a 30-fold reduced concentration.

In the next experiments the influence of PMA (phorbol-12-myristate-13-acetate) has been examined.

Different PMA concentrations in combination with single deposited cells of a non-immunized animal have been tested. The results are shown in the next Tables.

| c(PMA) [ng/ml] | Vitality [%] | | frequency/plate rbIgG+ [% total] | | average productivity/plate, IgG+ wells [µg/ml] | |
|---|---|---|---|---|---|---|
| | 4 Gy | 50 Gy | 4 Gy | 50 Gy | 4 Gy | 50 Gy |
| 0 | 50.4 | 0.4 | 59.1 | 50.8 | 3.90 | 0.98 |
| 0.015 | n.d. | n.d. | 54.0 | n.d. | 3.90 | n.d. |
| 0.03 | 54.8 | 3.9 | 55.6 | 52.4 | 3.90 | 1.36 |
| 0.06 | 45.4 | n.d. | 57.5 | n.d. | 3.72 | n.d. |
| 0.125 | 39.8 | n.d. | 56.0 | n.d. | 3.78 | n.d. |
| 0.25 | 34 | 9.5 | 64.3 | 54.4 | 3.83 | 2.48 |
| 0.5 | 32.2 | n.d. | 57.5 | n.d. | 4.06 | n.d. |
| 1.3 | 19.2 | 17.4 | 56.0 | 58.7 | 3.57 | 3.51 |

It can be seen that for 50 Gy irradiated EL-4 B5 cells a concentration dependent effect for the addition of PMA can be seen. In contrast thereto for 4 Gy irradiated EL-4 B5 cells no such effect is seen. Thus, in a concentration range of from 0.015 ng/ml to 1.3 ng/ml the PMA concentration has no influence on the frequency of IgG positive wells or the productivity The experiment was repeated with three HSA immunized rabbits. The respective results are presented in the following Tables.

frequency of IgG positive wells

| animal no. | 20,000 4 Gy irradiated EL-4 B5 cells/well PMA concentration [ng/ml] | | | | | 50,000 50 Gy irradiated EL-4 B5 cells/well |
|---|---|---|---|---|---|---|
| | 0 | 0.125 | 0.25 | 0.5 | 1 | 1.3 |
| 1 | -- | --- | +++++ | ++++ | ++++++ | - |
| 2 | --- | o | ++++ | + | ++++++ | +++ |
| 3 | + | ++++ | ++++++ | ++ | --- | ++++ | productivity of IgG positive wells

| animal no. | 20,000 4 Gy irradiated EL-4 B5 cells/well PMA concentration [ng/ml] | | | | | 50,000 50 Gy irradiated EL-4 B5 cells/well |
|---|---|---|---|---|---|---|
| | 0 | 0.125 | 0.25 | 0.5 | 1 | 1.3 |
| 1 | +++ | +++ | +++ | ++++ | ++++++ | --- |
| 2 | +++ | +++++ | ++++++ | +++ | --- | + |
| 3 | + | + | ++++++ | ++++++ | --- | ++++ | frequency of antigen specific wells of total wells

| animal no. | 20,000 4 Gy irradiated EL-4 B5 cells/well PMA concentration [ng/ml] | | | | | 50,000 50 Gy irradiated EL-4 B5 cells/well |
|---|---|---|---|---|---|---|
| | 0 | 0.125 | 0.25 | 0.5 | 1 | 1.3 |
| 1 | o | --- | ++++ | ++++++ | +++++ | -- |
| 2 | --- | o | +++ | + | ++ | ++++++ |
| 3 | o | o | ++++++ | +++++ | --- | +++++ | frequency of antigen specific wells of IgG positive wells

| animal no. | 20,000 4 Gy irradiated EL-4 B5 cells/well PMA concentration [ng/ml] | | | | | 50,000 50 Gy irradiated EL-4 B5 cells/well |
|---|---|---|---|---|---|---|
| | 0 | 0.125 | 0.25 | 0.5 | 1 | 1.3 |
| 1 | | --- | +++ | +++++ | - | - |
| 2 | --- | o | +++ | + | o | ++++++ |
| 3 | -- | --- | ++++++ | +++ | + | o |

IgG+ Frequency [% total wells]

| PMA [ng/ml] | 15k/Well | 20k/Well | | 50k/Well | |
|---|---|---|---|---|---|
| | 3 Gy | 4 Gy | 5 Gy | 8 Gy | 50 Gy |
| 1.3 | 8.3 | 72.6 | 84.5 | 88.1 | 83.3 |
| 0.57 | 32.1 | 72.6 | 86.9 | 81 | 84.5 |
| 0.25 | 47.6 | 75 | 84.5 | 88.1 | 20.2 |
| 0.109 | 47.6 | 76.2 | 83.3 | 77.4 | 16.7 |
| 0.048 | 48.8 | 73.8 | 71.4 | 84.5 | 14.3 |

Average IgG Productivity of all IgG+ wells [µg/ml]

| | 15k/Well | 20k/Well | | 50k/Well | |
|---|---|---|---|---|---|
| | 3 Gy | 4 Gy | 5 Gy | 8 Gy | 50 Gy |
| 1.3 | 4.937 | 5.011 | 4.8 | 5.198 | 5.427 |
| 0.57 | 6.067 | 5.834 | 5.269 | 5.72 | 4.876 |
| 0.25 | 3.094 | 4.61 | 5.313 | 5.945 | 1.893 |
| 0.109 | 2.932 | 5.772 | 5.335 | 5.614 | 1.942 |
| 0.048 | 1.405 | 5.465 | 5.769 | 5.739 | 2.821 |

HSA (absolute corrected) Freq./plate OD>c [% total]

|  | 15k/Well | 20k/Well | | 50k/Well | |
| --- | --- | --- | --- | --- | --- |
|  | 3 Gy | 4 Gy | 5 Gy | 8 Gy | 50 Gy |
| 1.3 | 3.6 | 31 | 34.5 | 36.9 | 40.5 |
| 0.57 | 11.9 | 26.2 | 38.1 | 35.7 | 40.5 |
| 0.25 | 21.4 | 33.3 | 32.1 | 32.1 | 13.1 |
| 0.109 | 9.5 | 32.1 | 42.9 | 32.1 | 9.5 |
| 0.048 | 25 | 36.9 | 27.4 | 42.9 | 14.3 |

HSA (absolute corrected) Freq./plate OD>c and rbIgG+ [% IgG]

|  | 15k/Well | 20k/Well | | 50k/Well | |
| --- | --- | --- | --- | --- | --- |
|  | 3 Gy | 4 Gy | 5 Gy | 8 Gy | 50 Gy |
| 1.3 | 42.9 | 42.6 | 40.8 | 40.5 | 47.1 |
| 0.57 | 33.3 | 36.1 | 43.8 | 44.1 | 46.5 |
| 0.25 | 45 | 44.4 | 38 | 36.5 | 47.1 |
| 0.109 | 17.5 | 42.2 | 47.1 | 41.5 | 50 |
| 0.048 | 48.8 | 50 | 38.3 | 49.3 | 58.3 |

It can be seen that the advantageous PMA concentration range when taking the parameters frequency of IgG positive wells, productivity and frequency of wells producing antigen specific IgG is in the range between 0.1 ng/ml to 0.5 ng/ml PMA for a CM fraction of 0.03, preferably in the range of 0.25 ng/ml to 0.5 ng/ml, when using EL-4 B5 cells irradiated with 0 to 8 Gy.

The results obtained with 5,000 non-irradiated EL-4 B5 cells per well per single deposited B-cell is shown in the following Tables.

frequency per plate of rbIgG-positive wells [% total]

| PMA | w/o irradiation = 0 Gy | | | | |
| --- | --- | --- | --- | --- | --- |
| [ng/ml] | 2x CM | 1x CM | 0.31x CM | 0.1x CM | 0.031x CM |
| 0.73 | 48.8 | 36.9 | 67.9 | 75.0 | 76.2 |
| 0.43 | 45.2 | 50.0 | 71.4 | 72.6 | 67.9 |
| 0.25 | 48.8 | 65.5 | 73.8 | 54.8 | 53.6 |
| 0.14 | 54.8 | 69.0 | 54.8 | 52.4 | 35.7 |
| 0.08 | 65.5 | 65.5 | 51.2 | 44.0 | 39.3 | average productivity per plate of rbIgG-positive wells [% total]

| PMA | w/o irradiation = 0 Gy | | | | |
| --- | --- | --- | --- | --- | --- |
| [ng/ml] | 2x CM | 1x CM | 0.31x CM | 0.1x CM | 0.031x CM |
| 0.73 | 0.508 | 0.806 | 2.421 | 4.197 | 4.153 |
| 0.43 | 1.426 | 1.440 | 2.989 | 2.651 | 1.467 |
| 0.25 | 1.026 | 1.890 | 1.513 | 1.036 | 0.465 |
| 0.14 | 1.192 | 1.635 | 0.771 | 0.621 | 0.340 |
| 0.08 | 1.221 | 1.590 | 0.665 | 0.385 | 0.394 |

The following examples are provided to aid the understanding of the present invention, the true scope of which is set forth in the appended claims. It is understood that modifications can be made in the procedures set forth without departing from the spirit of the invention.

EXAMPLES

Materials and Methods
Recombinant DNA Techniques

Standard methods were used to manipulate DNA as described in Sambrook, J., et al., Molecular Cloning: A Laboratory Manual, Cold Spring Harbor Laboratory Press, Cold Spring Harbor, N.Y. (1989). The molecular biological reagents were used according to the manufacturer's instructions.

Cytokines

Zubler Mix: 2 ng/ml mouse IL-1B, 50 ng/ml mouse IL-2, 10 ng/ml mouse IL-10, and 2 ng/ml mouse TNFα (final concentration)

Cytokines:

| cytokine | supplier | Catnr. |
| --- | --- | --- |
| huIL-2 | Roche Dia. GmbH | 11147528001 |
| muIL-2 | Miltenyi Biotec | 130-094-055 |
| huIL-6 | Roche Dia. GmbH | 11138600001 |
| muIL-6 | Miltenyi Biotec | 130-096-684 |
| huIL-10 | BD | 554611 |
| muIL-10 | Miltenyi Biotec | 130-094-068 |
| huIL-1β | R&Dsystems | 201-LB |
| muIL-1β | Miltenyi Biotec | 130-101-682 |
| huTNF-α | R&Dsystems | 210-TA |
| muTNF-α | Miltenyi Biotec | 130-101-690 |

Rabbit B-Cell Medium

| 500 ml | RPMI 1640 | #P04-17500 | PAN Biotech |
| --- | --- | --- | --- |
| 10% | FCS | #P30-1900 | PAN Biotech |
| 1x | L-Glu/Pen/Strep (100x) | #10378-016 | Gibco |
| 2 mM | sodium pyruvate | #P04-43100 | PAN Biotech |
| 10 mM | HEPES | #P05-0110 | PAN Biotech |
| 0.05 mM | β-mercaptoethanol | # 31350-010 | Invitrogen |

Additives to Rabbit B-Cell Medium

| SAC | #507858 | Calbiochem |
| --- | --- | --- |
| TSN or | 605911 | Microcoat |
| Cytokine Mix | (see above) | |
| PMA | #P8139 | Sigma |
| 96er U-plate | #168136 | Nunc |

Phenotyping/Sorting of Antibodies

| goat anti-rabbit IgG Fc-antibody | AbDSerotec | STAR121F |
| --- | --- | --- |
| donkey anti-goat IgG antibody Alexa 488 | Molecular Probes | A11055 |

Example 1

Animal Care and Immunization

NZW rabbits obtained from Charles River Laboratories International, Inc. were used for immunization. The animals were housed according to the Appendix A "Guidelines for accommodation and care of animals" in an AAALACi accredited animal facility. All animal immunization protocols and experiments were approved by the Government of Upper Bavaria (permit number 55.2-1-54-2532-90-14) and performed according to the German Animal Welfare Act and the Directive 2010/63 of the European Parliament and Council.

NZW rabbits, 12-16 week old, were immunized either with recombinant human serum albumin protein (HSA; CAS RN 70024-90-7; Sigma) or recombinant VEGF-KLH protein.

One set of rabbits was immunized with 400 μg HSA, emulsified with complete Freund's adjuvant, at day 0 by intradermal application, followed by 200 μg HSA emulsified with complete or incomplete Freund's adjuvant at weeks 1, 2, 6, 10 and 23, by alternating intramuscular and subcutaneous injections.

For the immunization with VEGF-KLH 400 μg antigen, emulsified with complete Freund's adjuvant, at day 0 by intradermal application, followed by 200 μg VEGF-KLH emulsified with complete Freund's adjuvant at weeks 1, 2, 7 and 10, by alternating intramuscular and subcutaneous injections.

Blood (10% of estimated total blood volume) was taken at days 4, 5 and 6 post immunizations, starting from the 3rd immunization onwards. Serum was prepared for immunogen-specific IgG titer determination by ELISA.

Example 2

Removal of Blood (Immunized and Non-Immunized Rabbits)

Generally, blood from rabbits was obtained by punctuation of the ear vein or, for larger volumes, of the ear artery. From immunized rabbits, whole blood containing EDTA (16 ml) was collected 4-6 days after the third, fourth, fifth and sixth immunization and used for single cell sorting by FACS.

Example 3

Isolation of Peripheral Blood Mononuclear Cells (PBMCs)

The isolation of peripheral blood mononuclear cells (PBMCs) was performed by density gradient separation with Lympholyte® according to manufacturer's instructions A (Lympholyte®-mammal, Cedarlane).

Withdrawn blood was diluted 1:2 with phosphate buffered saline (PBS). In a centrifuge tube the recommended volume of density separation medium was carefully overlaid with the diluted blood. The vial was centrifuged for 20 min. at 800×g without brake. The lymphocytes were obtained from the white interim layer. The removed cells were washed twice with PBS and centrifugation at 800×g for 10 min.

Sterile 6-well plates (cell culture grade) were used to deplete macrophages and monocytes through unspecific adhesion. Wells were either uncoated or coated with KLH (keyhole limpet haemocyanine) or with streptavidin. Each well was filled with 1 ml to (at maximum) 2 ml medium and up to 6×10$^6$ peripheral blood mononuclear cells from the immunized rabbit and allowed to bind for 60 to 90 min. at 37° C. in the incubator. Thereafter the lymphocyte containing supernatant was transferred to a centrifugation vial and centrifuged at 800×g for 10 min. The pellet was resuspended in medium.

Example 4

Enrichment of Antigen-Specific B-Cells

The antigen was diluted with coating buffer to a final concentration of 2 μg/ml. 4 ml of this solution were added to the well of a 6-well multi well plate and incubated over night at room temperature. Prior to use the supernatant was removed and the wells were washed three-times with PBS. Each well was filled with 1 ml to (at maximum) 2 ml medium and up to 6×10$^6$ peripheral blood lymphocytes. The plate was incubated for 60 min at 37° C. The supernatant was discarded. Non-adherent cells were removed by carefully washing the wells 1-4 times with 1×PBS. For recovery of the sticky antigen-specific B-cells 1 ml of a trypsin/EDTA-solution was added to the wells of the multi well plate and incubated for 5 to 10 min. at 37° C. The incubation was stopped by addition of medium and the supernatant was transferred to a centrifugation vial. The wells were washed twice with medium and the supernatants were combined with the other supernatants. The cells were pelleted by centrifugation for 10 min. at 800×g. The cells were kept on ice until the immune fluorescence staining. The pellet was optionally resuspended in PBS.

Example 5

Production of Thymocyte Supernatant (TSN)
Procedure 1:
Cultivation of T-Cells

T-cells were isolated from the thymus of 4-5 week old rabbits. The cells were centrifuged and immediately cultivated or frozen in aliquots of 3×10$^7$ cells. The thymocytes were seeded with a minimum cell density of 5×10$^5$ cells/ml of EL-4 B5 medium in 175 cm$^2$ culture flasks and incubated for 48 hours at 37° C.
Cultivation of Macrophages Blood mononuclear cells from rabbits were cultivated in EL-4 B5 medium at a cell density of at least 1×10$^5$ cells/ml in 175 cm$^2$ culture flasks for 1.5 hours at 37° C. Afterwards the medium was removed and non-attached cells were removed from the attached macrophages by washing with warm EL-4 B5 medium, followed by cultivation for 48 hours in 35 ml medium.
Co-Cultivation of T-Cells and Macrophages T-cells and macrophages were cultivated for 48 hours in separate flasks. Prior to combining both cell populations, the T-cells were centrifuged for 10 min. at 800×g. The supernatant was discarded and the cell pellet was resuspended in 10 ml medium. The T-cells were adjusted to a minimal cell density of 5×10$^5$ cells/ml and 10 ng phorbol-12-myristate-13-acetate (PMA) and 5 μg or 50 μg Phytohemagglutinin M (PHA-M) per ml of medium were added. The cultivation medium was removed from macrophages and the T-cell suspension was added to the flasks containing macrophages. After 36 hours of co-cultivation, the cultivation medium was removed and was termed TSN solution. For removal of remaining cells, the TSN solution was filtered through a 0.22 μm filter. The TSN solution was frozen at −80° C. in aliquots of 4 ml.
Procedure 2:
Cultivation of T-Cells The T-cells were isolated from the thymus of 3-4 week old mice and hamsters, or of 4-5 week old rabbits, respectively. The cells were centrifuged and immediately cultivated or frozen in aliquots of 4-5×10$^7$ cells. The thymocytes were seeded with a minimum cell density of 5×10$^5$ cells/ml of EL-4 B5 medium in 175 cm$^2$ culture flasks and incubated for up to 48 hours (40-48 hours depending on the TSN production method the macrophages will be used in; see Examples 9 and 10) at 37° C.
Cultivation of Macrophages Macrophages were isolated from the peritoneal cavity of mice and hamsters, respectively, of an age of at least three months. Peritoneal macrophages from mice or hamsters, or blood mononuclear cells from rabbits were cultivated in EL-4 B5 medium at a cell density of at least 1×10$^5$ cells/ml in 175 cm$^2$ culture flasks for 1.5 hours at 37° C. Afterwards the medium was removed and non-attached cells were removed from the attached macrophages by washing with warm EL-4 B5 medium, followed by cultivation for about 48 hours in 35 ml medium.
Co-Cultivation of T-Cells and Macrophages T-cells and macrophages were cultivated in separate flasks. Prior to combining both cell populations, the T-cells were centrifuged for 10 min. at 800×g. The supernatant was discarded and the cell pellet was resuspended in 10 ml EL-4

B5 medium. The final cultivation medium contained T-cells adjusted to a cell density of $5\times10^5$ cells/ml, 10 ng phorbol-12-myristate-13-acetate (PMA) per ml of medium, and 5 µg phytohemagglutinin M (PHA-M) per ml of medium (=T-cell suspension). Thereafter, the cultivation medium was removed from the macrophages (=medium-depleted macrophages). An amount/volume of the T-cell suspension was added to the flasks containing the medium-depleted macrophages to obtain a final but defined macrophage cell density of from $1.25-2\times10^6$ macrophages/ml. After 30-46 hours of co-cultivation, the cultivation medium was removed and was termed TSN solution. For removal of remaining cells, the TSN solution was filtered through a 0.22 µm filter. The TSN solution was frozen at −80° C. in aliquots (of 4.2 ml).

Example 6

Cultivation of EL-4 B5 Cells

Frozen EL-4 B5 cells were thawed rapidly in a water bath at 37° C. and diluted with 10 ml EL-4 B5 medium. After centrifugation at 300×g for 10 minutes the supernatant was discarded and the pellet resuspended in 1 ml medium.

The EL-4 B5 cells were inoculated at a cell density of $8\times10$ cells/ml in a T175 cultivation flasks. Cell density was determined every second day and adjusted to $8\times10^4$ cells/ml. The cells have a doubling time of approximately 18 hours.

After reaching a sufficient amount of cells and a density between 0.5 and $1-2\times10^6$ cells/ml cells were harvested and irradiated with a single dose of external radiation from a $^{137}$Cs source.

Two days after the irradiation only about one third and seven days after the irradiation on average only about 15% of the cells are vital, i.e. alive.

In more detail, EL-4 B5 cells have been expanded with the method as described in this Example. Before γ-irradiation the cell density was adjusted to $10\times10^6$ cells/ml. The used dose was 50 Gy. After the irradiation the cells were further cultivated in EL-4 B5 medium. Every day cell number and cell viability (using the ViCell device and trypan blue staining) were determined. The average vitality (relative number of living cells) at the respective days after the irradiation with 50 Gy gamma radiation is presented in the following Table (n=number of data points).

| days after irradiation | n | average viability [%] | SD/2 |
|---|---|---|---|
| 0 | 8 | 86.0 | 4.4 |
| 1 | 6 | 52.8 | 4.9 |
| 2 | 6 | 33.6 | 4.9 |
| 4 | 7 | 22.8 | 4.2 |
| 7 | 8 | 16.0 | 4.6 |

Example 7

Immunofluorescence Staining and Single Cell Deposition
Protocol 1:

Depending on the number of cells to be stained the cells were provided in 100 µl medium (less than $10^6$ cells) or 200 µl medium (more than $10^6$ cells), respectively. The fluorescent labeled antibody was diluted with 5% serum of the experimental animal and FACS buffer to a final volume of 100 µl or 200 µl, respectively. The reaction mixture was incubated on a roller rack for 40 min. at 4° C. in the dark. After the incubation the cells were washed twice at 300×g for 5 min. The pellet was resuspended in 400 µl PBS and filtered through a 70 µm sieve. The filtered solution was transferred to a FACS-vial and directly before the FACS experiment dead cells were stained by addition of propidium iodide (6.25 µg/ml). If the labeled antibody was labeled with biotin the antibody was detected in a second step with streptavidin labeled Alexa Flour® 647 (antibody 197).

Protocol 2:

Anti-rabbit IgG FITC used for single cell sorting was from AbD Serotec (STAR121F, Dusseldorf, Germany).

For surface staining, cells were incubated with the optimally diluted anti-rabbit IgG FITC antibody in FACS buffer for 30 min. with rolling at 4° C. in the dark. Following centrifugation, the supernatants were removed by aspiration. The PBMCs were subjected to two cycles of centrifugation and washing with ice cold PBS. Finally, the PBMCs were resuspended in ice cold PBS and immediately subjected to the FACS analyses. Propidium iodide in a concentration of 5 µg/ml (BD Pharmingen, San Diego, Calif., USA) was added prior to the FACS analyses to discriminate between dead and live cells. In other experiments the stained cells were single deposited by FACS.

A Becton Dickinson FACSAria equipped with a computer and the FACSDiva software (BD Biosciences, USA) were used to collect and analyze the data.

FACS-buffer for immuno fluorescence staining comprises 1×PBS and 0.1% BSA.

Example 8

Co-Cultivation of B-Cells and EL-4 B5 Cells

Single cell sorted B-cells were cultured in 96-well plates with 200 µl/well EL-4 B5 medium with Pansorbin Cells (SAC) (Calbiochem (Merck), Darmstadt, Deutschland), EL-4 B5 cells ($0-5\times10^4$/well) and rabbit thymocyte supernatant or cytokine mix, respectively, for 7 days at 37° C. in an atmosphere of 5% $CO_2$ in the incubator. B-cell culture supernatants were removed for screening and the cells harvested immediately for variable region gene cloning or frozen at −80° C. in 100 µl RLT buffer (Qiagen, Hilden, Germany).

Example 9

Quantification of IgG

A mixture of 0.5 µg/ml of biotinylated mouse anti-rabbit IgG antibody (Sigma-Aldrich) and 0.35 µg/ml anti-rabbit IgG HRP conjugate (Sigma-Aldrich) was transferred to 384 well streptavidin coated microtiter plates (MicroCoat Biotechnologie GmbH). Dilutions of B-cell supernatants in PBS supplemented with 0.5% BSA and 0.05% Tween®-20 were added and incubated for 90 min at RT. After repeated washing (6×) with PBST (phosphate buffered saline with 0.2% Tween buffer the plates were developed with BM Blue® HRP substrate solution and color formation was measured by absorbance at 370 nm. A commercial rabbit IgG (Sigma-Aldrich) was used as a calibration standard.

Example 10

Antigen Binding Immunoassay

The assay was performed at room temperature (RT) on 384-well MaxiSorp microtiter plates (Thermo Scientific) with PBS (phosphate buffered saline) buffer supplemented with 0.5% Gelatin and 0.025% Tween®-20. The plates were coated with 0.5 µg/ml of human serum albumin (HSA, Sigma-Aldrich) for at least 2 hours to overnight. After washing (3×) with PBST (PBS with 0.1% Tween®-20) buffer the wells were blocked with PBS with 0.5% Gelatin and 0.1% Tween®-20. Again, the plates were washed three-times and afterwards dilutions of B-cell supernatants were added. After an incubation of 60 min and 3 washing steps with PBST a 1:4,000 dilution of a HRP-conjugated anti-rabbit IgG antibody (Amersham) was transferred to the wells and incubated for 60 min. Finally, the plates were repeatedly washed (6×) with PBST and developed with BM Blue® HRP substrate solution for 30 min. Absorbance was measured at 392-405 nm.

What is claimed is:

1. A method for cultivating one or more B-cells comprising the step of co-cultivating one or more B-cells with EL-4 B5 cells,
   wherein the EL-4 B5 cells have been irradiated prior to the co-cultivation with a dose of 9.5 Gy or less but greater than 0 Gy, and
   wherein the number of EL-4 B5 cells at the start of the co-cultivating is less than $5 \times 10^4$ per B-cell.

2. The method according to claim 1, wherein the co-cultivating is additionally in the presence of a feeder mix.

3. The method according to claim 2, wherein the feeder mix comprises one or more of
   i) interleukin-1 beta and tumor necrosis factor alpha,
   ii) interleukin-2 (IL-2) and/or interleukin-10 (IL-10),
   iii) *Staphylococcus aureus* strain Cowan's cells (SAC),
   iv) interleukin-21 (IL-21) and optionally interleukin-2 (IL-2),
   v) B-cell activation factor of the tumor necrosis factor family (BAFF),
   vi) interleukin-6 (IL-6),
   vii) interleukin-4 (IL-4), and
   viii) thymocyte cultivation supernatant.

4. The method according to claim 3, wherein the feeder mix comprises about 2 ng/ml (murine) IL-1beta,
about 2 ng/ml (murine) TNFalpha,
about 50 ng/ml (murine) IL-2,
about 10 ng/ml (murine) IL-10, and
about 10 ng/ml (murine) IL-6,
or a fraction thereof.

5. The method according to claim 4, wherein the fraction of the feeder mix is in the range of from 1.0- to 0.015-times of each of said concentrations of IL-1beta, TNFalpha, IL-2, IL-10, and IL-6.

6. The method according to claim 3, wherein the feeder mix further comprises phorbol myristate acetate.

7. The method according claim 2, wherein the method is for the cultivation of a single deposited B-cell.

8. The method according to claim 7, wherein the co-cultivating is for 5 to 10 days.

9. The method according to claim 1, wherein the co-cultivating of the one or more B-cells is with about 10,000 to about 30,000 EL-4 B5 cells, which have been irradiated with gamma radiation of a dose in the range of about 3 Gy to about 6 Gy.

10. The method according to claim 1, wherein the co-cultivating of the one or more B-cells is with about 10,000 to about 30,000 EL-4 B5 cells, which have been irradiated with gamma radiation of the dose in the range of about 3 Gy to about 6 Gy, wherein the feeder mix comprises about 0.06 ng/ml IL-1beta, about 0.06 ng/ml TNFalpha, about 1.5 ng/ml IL-2, about 0.3 ng/ml IL-10, about 0.3 ng/ml IL-6, and about 0.25 ng/ml-0.5 ng/ml PMA.

11. The method according to claim 2, wherein the co-cultivating of the one or more B-cells is with about 2,500 to about 7,500 EL-4 B5 cells, which have been irradiated with gamma radiation of a dose less than 3 Gy.

12. The method according to claim 1, wherein the co-cultivating of the one or more B-cells is with about 2,500 to about 7,500 EL-4 B5 cells, which have been irradiated with gamma radiation of a dose less than 3 Gy, wherein the feeder mix comprises about 0.06 ng/ml to about 0.2 ng/ml IL-1beta, about 0.06 ng/ml to about 0.2 ng/ml TNFalpha, about 1.5 ng/ml to about 5 ng/ml IL-2, about 0.3 ng/ml to about 1 ng/ml IL-10, about 0.3 ng/ml to about 1 ng/ml IL-6, and about 0.43 ng/ml-0.73 ng/ml PMA.

13. The method according to claim 5, wherein the feeder mix further comprises about 0.125 ng/ml-1 ng/ml phorbol myristate acetate.

14. The method according to claim 13, wherein the method is for the cultivation of a single deposited B-cell.

15. The method according to claim 14, wherein the co-cultivating is for 5 to 10 days.

16. The method according to claim 8, wherein the co-cultivating of the one or more B-cells is with about 10,000 to about 30,000 EL-4 B5 cells, which have been irradiated with gamma radiation of a dose in the range of about 3 Gy to about 6 Gy.

17. The method according to claim 16, further wherein the feeder mix comprises about 0.06 ng/ml IL-1beta, about 0.06 ng/ml TNFalpha, about 1.5 ng/ml IL-2, about 0.3 ng/ml IL-10, about 0.3 ng/ml IL-6, and about 0.25 ng/ml-0.5 ng/ml PMA.

18. The method according to claim 15, wherein the co-cultivating of the one or more B-cells is with about 2,500 to about 7,500 EL-4 B5 cells, which have been irradiated with gamma radiation of a dose less than 3 Gy.

19. The method according to claim 11, wherein the feeder mix comprises about 0.06 ng/ml to about 0.2 ng/ml IL-1beta, about 0.06 ng/ml to about 0.2 ng/ml TNFalpha, about 1.5 ng/ml to about 5 ng/ml IL-2, about 0.3 ng/ml to about 1 ng/ml IL-10, about 0.3 ng/ml to about 1 ng/ml IL-6, and about 0.43 ng/ml-0.73 ng/ml PMA.

20. The method according to claim 15, wherein the co-cultivating of the one or more B-cells is with about 2,500 to about 7,500 EL-4 B5 cells, which have been irradiated with gamma radiation of a dose less than 3 Gy, wherein the feeder mix comprises about 0.06 ng/ml to about 0.2 ng/ml IL-1beta, about 0.06 ng/ml to about 0.2 ng/ml TNFalpha, about 1.5 ng/ml to about 5 ng/ml IL-2, about 0.3 ng/ml to about 1 ng/ml IL-10, about 0.3 ng/ml to about 1 ng/ml IL-6, and about 0.43 ng/ml-0.73 ng/ml PMA.

* * * * *